(12) United States Patent
Rubin et al.

(10) Patent No.: US 9,540,336 B2
(45) Date of Patent: Jan. 10, 2017

(54) THERAPEUTIC AGENTS

(71) Applicant: THE TRUSTEES OF THE UNIVERSITY OF PENNSYLVANIA, Philadelphia, PA (US)

(72) Inventors: Harvey Rubin, Philadelphia, PA (US); Takahiro Yano, Narberth, PA (US); Sacha Kassovska-Bratinova, Havertown, PA (US); Norman Schechter, Philadelphia, PA (US); Jiah Shin Teh, Baltimore, MD (US); Jeffrey Winkler, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 14/366,879

(22) PCT Filed: Dec. 21, 2012

(86) PCT No.: PCT/US2012/071179
§ 371 (c)(1),
(2) Date: Jun. 19, 2014

(87) PCT Pub. No.: WO2013/096735
PCT Pub. Date: Jun. 27, 2013

(65) Prior Publication Data
US 2014/0371228 A1    Dec. 18, 2014

Related U.S. Application Data

(60) Provisional application No. 61/579,463, filed on Dec. 22, 2011.

(51) Int. Cl.
C07D 241/46    (2006.01)
A61K 31/50     (2006.01)
A61K 31/498    (2006.01)

(52) U.S. Cl.
CPC .......... *C07D 241/46* (2013.01); *A61K 31/498* (2013.01)

(58) Field of Classification Search
CPC ........................ A61K 31/498; C07D 241/48
(Continued)

(56) References Cited

U.S. PATENT DOCUMENTS 5,763,443 A    6/1998  Medlen et al.
2010/0330156 A1  12/2010 Liu et al.

FOREIGN PATENT DOCUMENTS

EP    0374991    6/1990

OTHER PUBLICATIONS

O'Sullivan et al. "Clofazimine Analogus Active against a Clofazimine-Resistant Organism," J. Med. Chem. 1988, vol. 31, pp. 567-572.*

(Continued)

*Primary Examiner* — Shengjun Wang
(74) *Attorney, Agent, or Firm* — Saul Ewing LLP; Kathryn Doyle; Domingos Silva

(57) ABSTRACT

The present invention includes a method of treating or preventing a disease or disorder such as a mycobacterial infection, a Gram-positive bacterium infection, a yeast infection, an inflammatory condition, an auto-immune disorder and/or a proliferative disorder in a subject in need thereof. The method comprises administering to the subject a therapeutically effective amount of at least one compound of the invention, which includes clofazimine derivatives.

11 Claims, 30 Drawing Sheets

CFZ: R = CH(CH₃)₂

(58) Field of Classification Search
USPC .................................. 514/250; 544/347, 348
See application file for complete search history.

(56) References Cited

OTHER PUBLICATIONS

PubChem CID 473704; http://pubchem.ncbi.nlm.nih.gov/summary/summary.cgi?cid+473704. Retrieved Apr. 22, 2013. Create Date Aug. 1, 2005.
PubChem CID 44368767; http://pubchem.ncbi.nlm.nih.gov/summary/summary.cgi?q=all&cid=44368767#ec. Retrieved Apr. 22, 2013. Create Date Nov. 19, 2009.
International Search Report dated May 2, 2013 for PCT International Application No. PCT/US12/71179.
PCT International Search Report and Written Opinion for PCT/US2012/071179 issued May 2, 2013.
PubChem CID 44368767; ps://pubchem.ncbi.nlm.nih.gov/summary/summary.cgi?q-all&cid=44368767#ec. Create Date: Nov. 19, 2009, Retrieved Apr. 22, 2013.
PubChem CID 473704; https://pubchem.ncbi.nlm.nih.gov/summary/summary.cgi?cid=473704. Create Date: Aug. 1, 2005, Retrieved Apr. 22, 2013.
Yano, et al., "Reduction of clofazimine by mycobacterial type 2 NADH:quinone oxidoreductase: a pathway for the generation of bactericidal levels of reactive oxygen species", J Biol Chem. 286(12), Mar. 25, 2011, 10276-10287.

* cited by examiner

CFZ: R = CH(CH₃)₂

Fig. 2
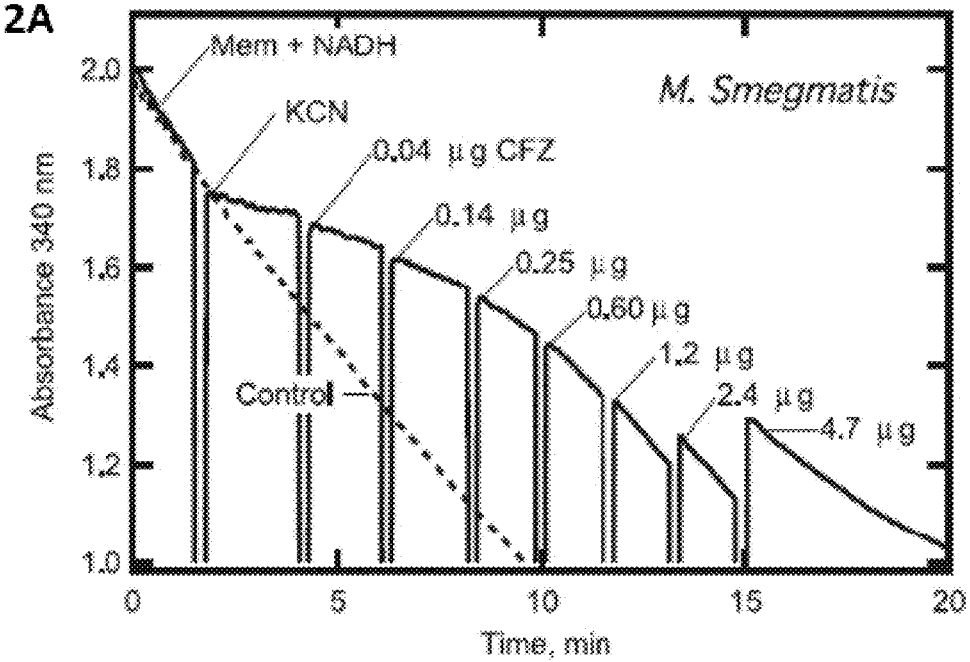
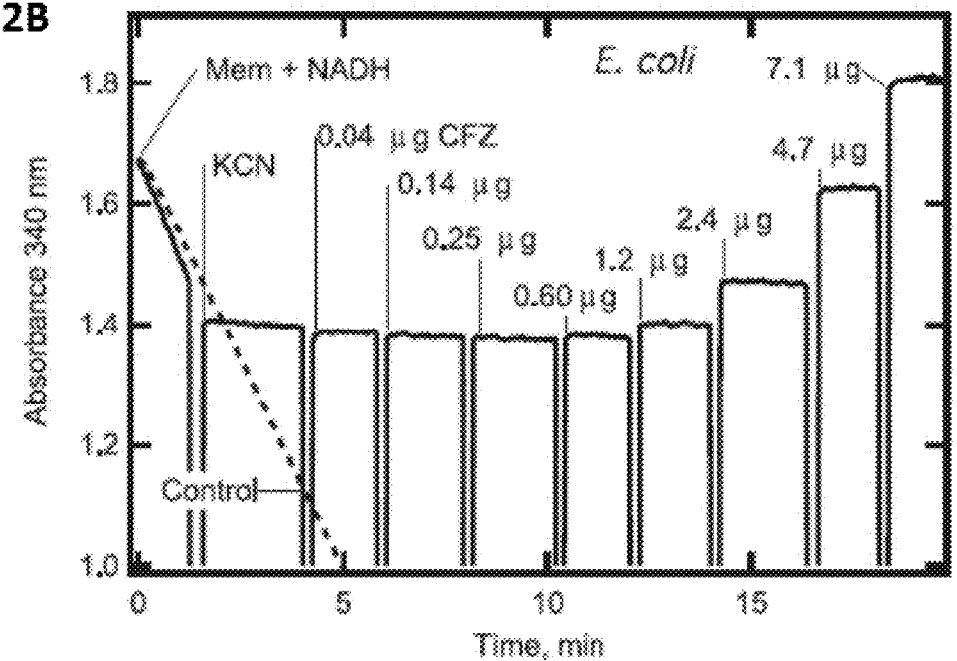

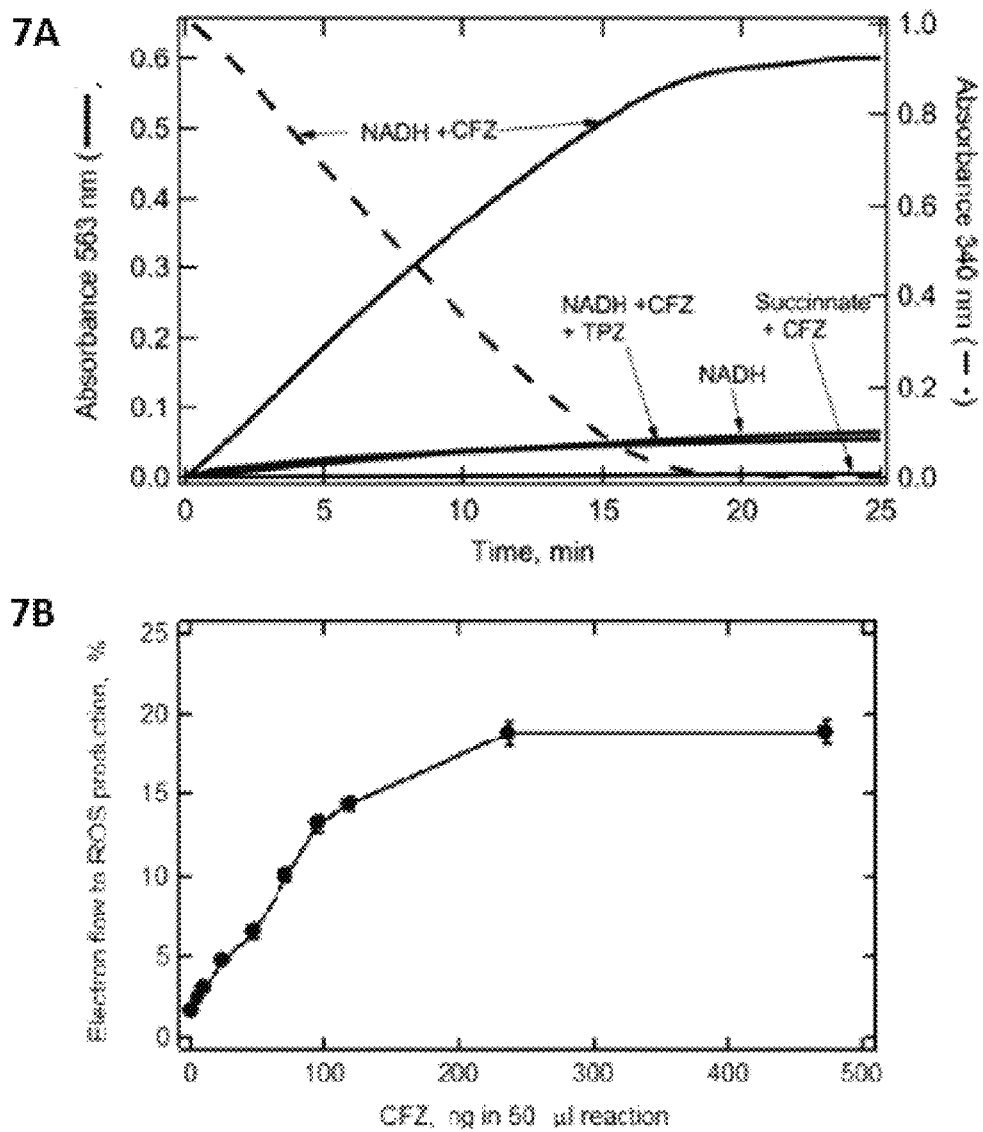

Fig. 8
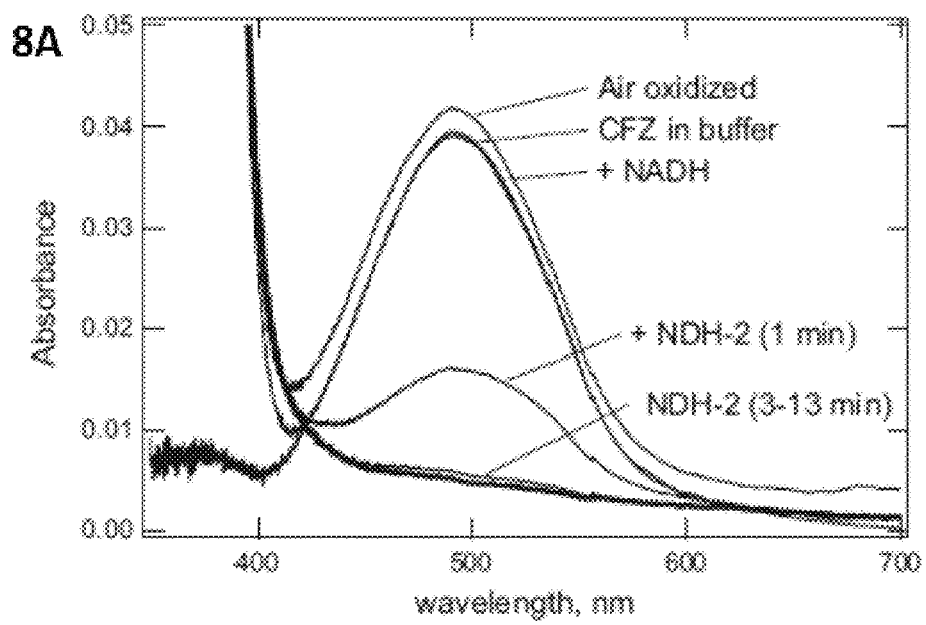
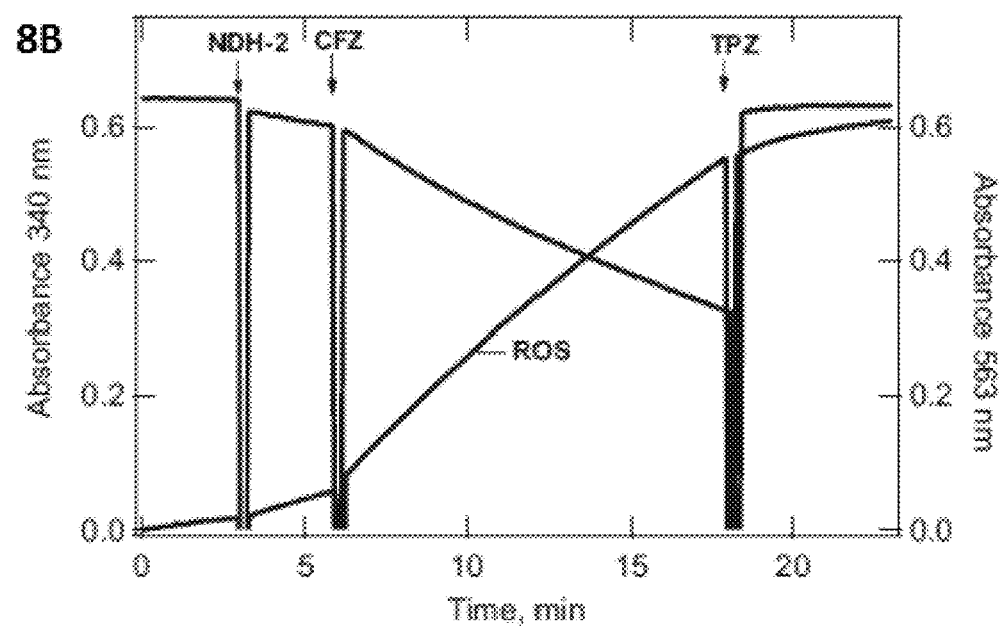

Fig. 10
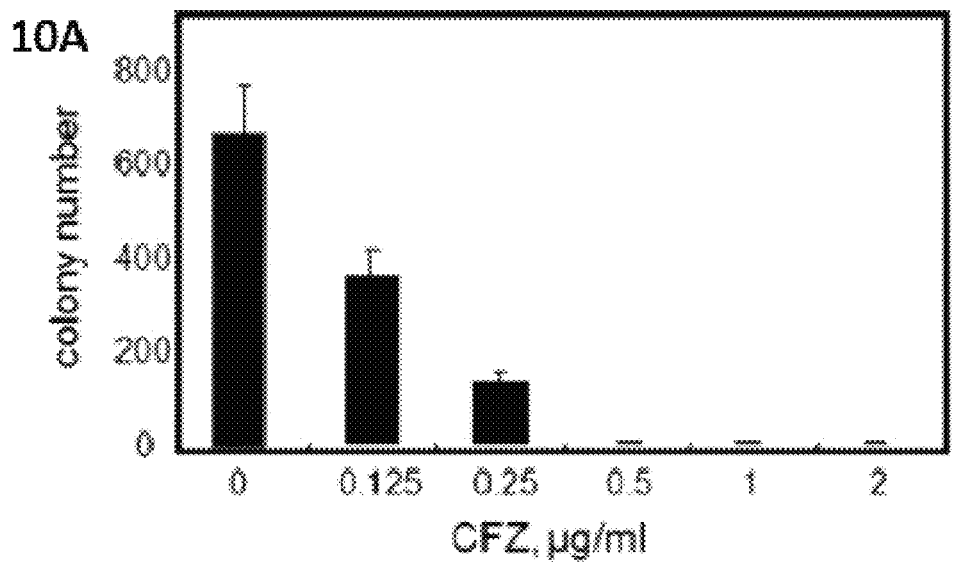
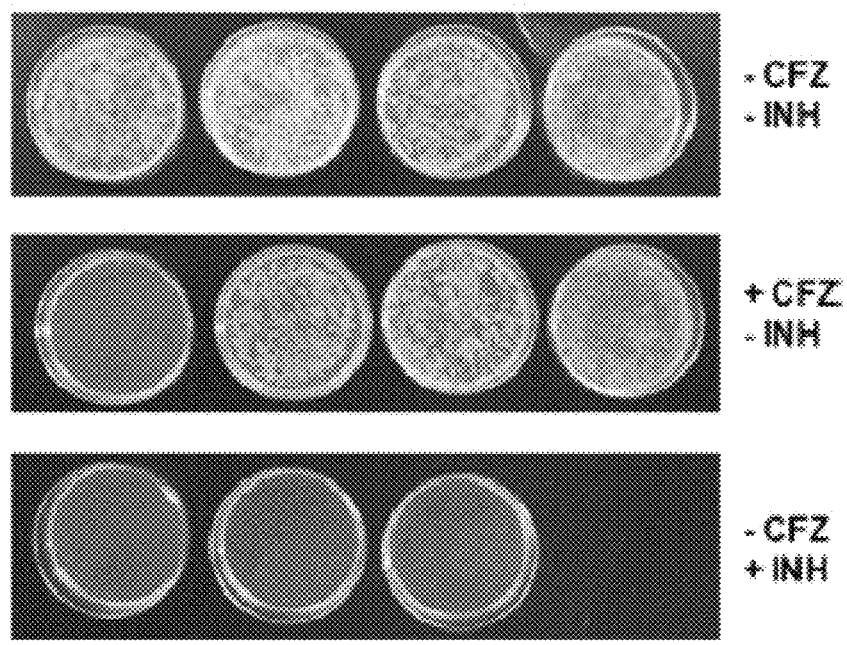

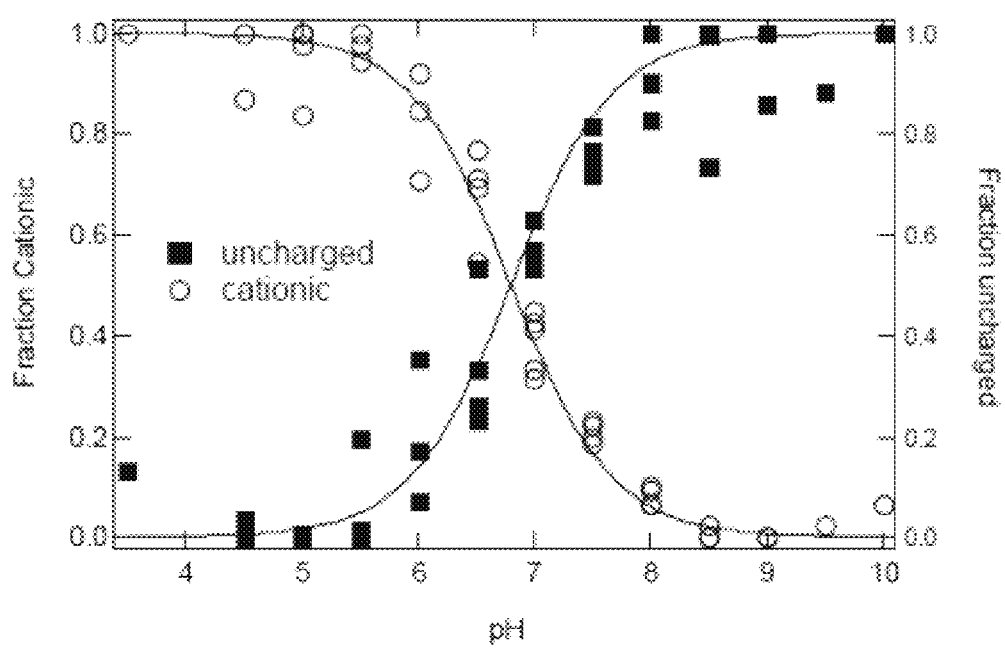

Fig. 15
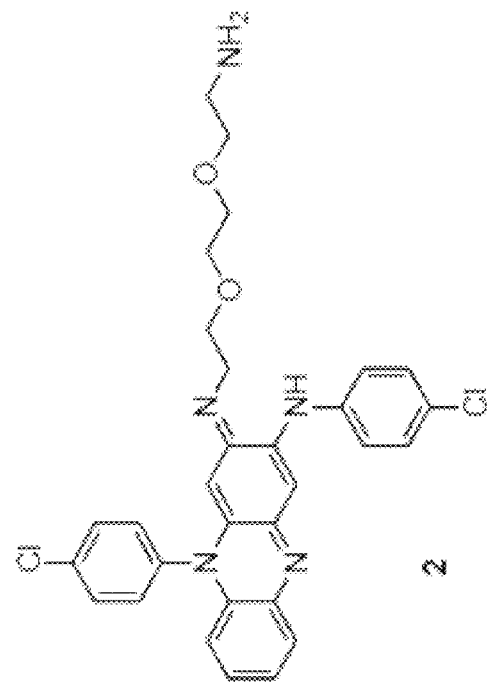
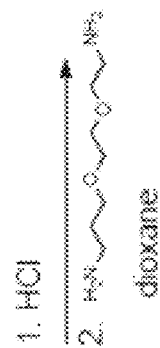
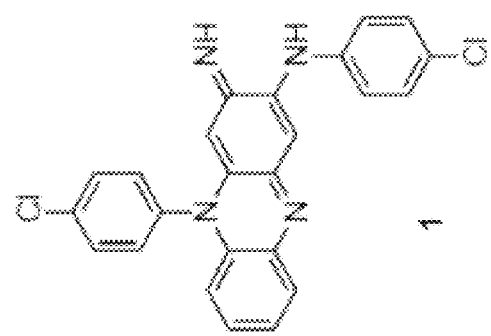

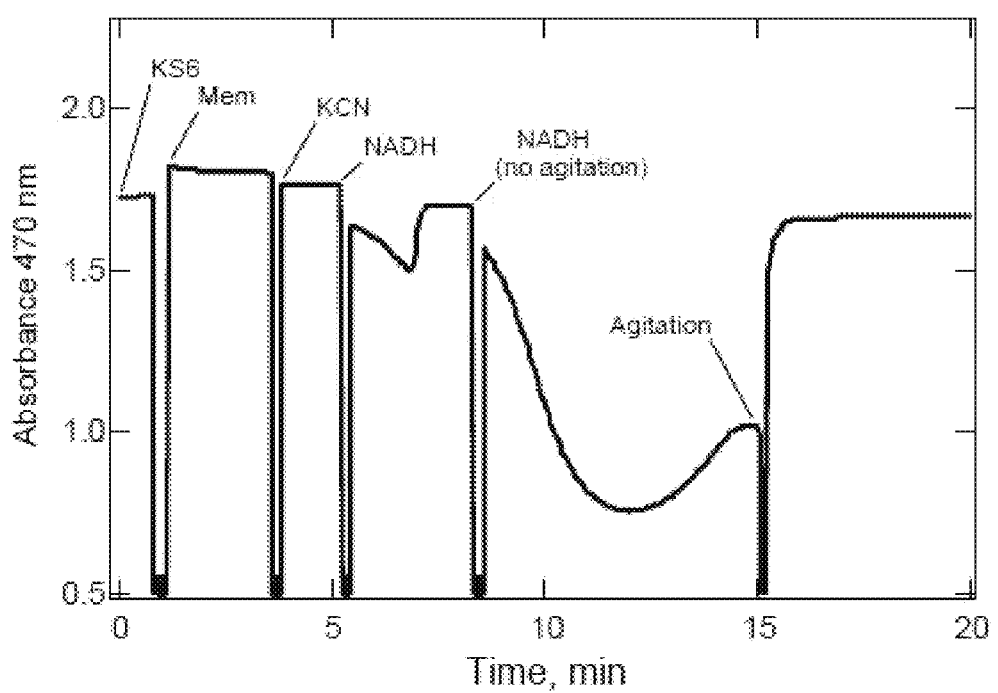

Fig. 19A
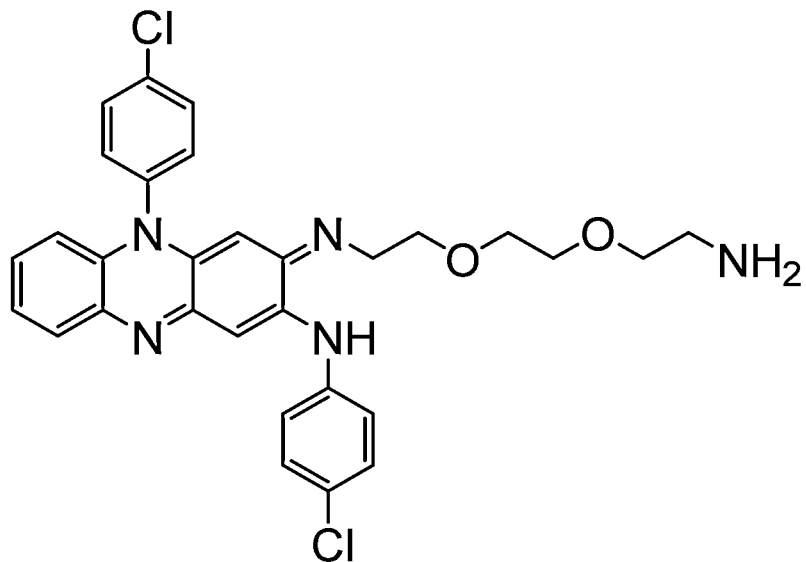
3 (KS6) MW 562; cLogP 6.61
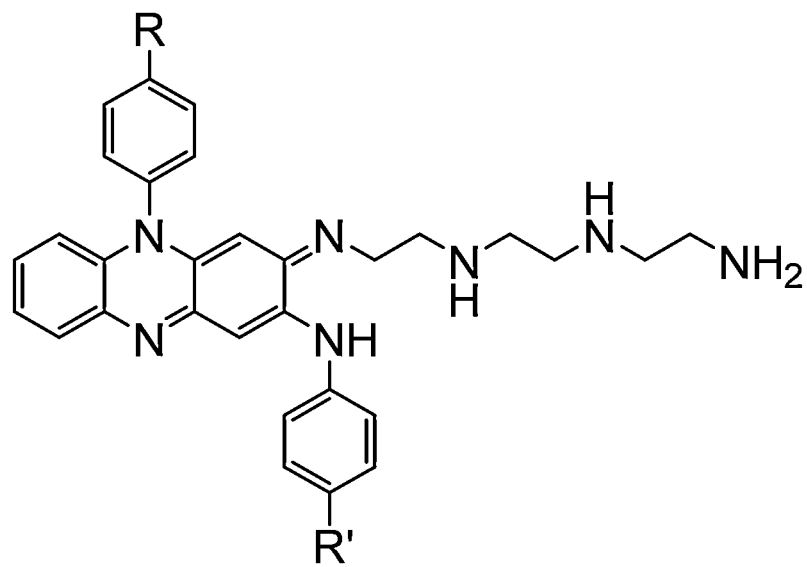
4 R=R'=Cl MW 560; cLogP 6.0
5 R=R'=H MW 491; cLogP 4.5

Fig. 19B
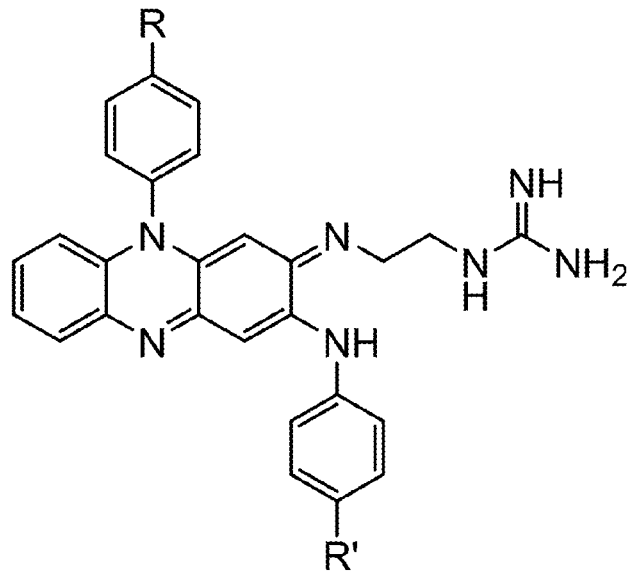
6 R=R'=Cl   MW 516; cLogP 6.0
7 R=R'=H    MW 447; cLogP 4.6
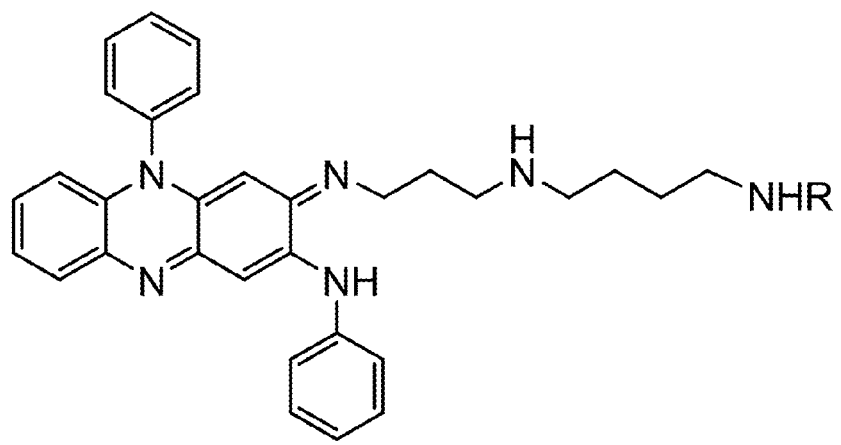
8 R= H                MW 490; cLogP 5.4
9 R= C(C=NH)NH$_2$  MW 532; cLogP 4.6

Fig. 19C
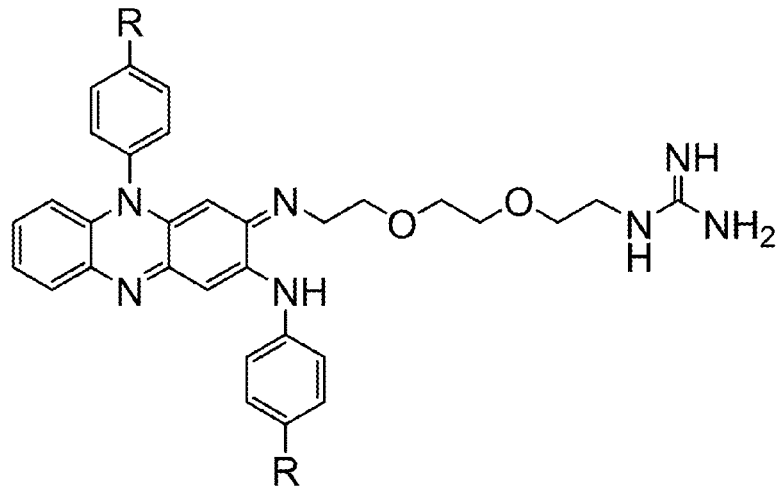
| | | |
|---|---|---|
| 10 | R=Cl | MW 604; cLogP 5.99 |
| 11 | R=NO$_2$ | MW 625; cLogP 4.2 |
| 12 | R=H | MW 535; cLogP 2.2 |
| 13 | R=COOH | MW 623; cLogP 1.8 |
| 14 | R=CONH$_2$ | MW 621; cLogP 1.7 |
| 15 | R=OH | MW 568; cLogP 3.5 |
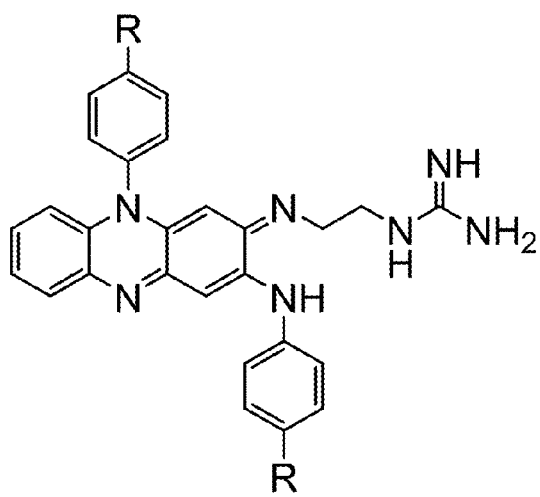
| | | |
|---|---|---|
| 16 | R=NO$_2$ | MW 537; cLogP 4.3 |
| 17 | R=COOH | MW 535; cLogP 1.9 |
| 18 | R=CONH$_2$ | MW 533; cLogP 1.7 |
| 19 | R=CONHMe | MW 561; cLogP 2.2 |
| 20 | R=OH | MW 479; cLogP 3.5 |

THERAPEUTIC AGENTS

CROSS-REFERENCE TO RELATED APPLICATIONS

The present application is a 35 U.S.C. §371 national phase application of, and claims priority to, PCT Application No. PCT/US2012/071179, filed Dec. 21, 2012, which claims priority to U.S. Provisional Patent Application No. 61/579,463, filed Dec. 22, 2011, all of which applications are incorporated herein by reference in their entireties.

STATEMENT REGARDING FEDERALLY SPONSORED RESEARCH OR DEVELOPMENT

This invention was made with government support under grant number Grant R01-AI068942-02, awarded by the National Institutes of Health. The government has certain rights in the invention.

BACKGROUND OF THE INVENTION

*Mycobacterium* is a genus of Actinobacteria, with its own family—the Mycobacteriaceae. There are more than 70 species of mycobacteria, with characteristic rod-like shapes and waxy outer coats. Tuberculosis (*Mycobacterium tuberculosis*) and leprosy (Hansen's disease; *Mycobacterium leprae*) are the best known mycobacterial diseases. Hosts may be colonized by mycobacteria without showing any adverse signs. For example, billions of people around the world have asymptomatic infections of *Mycobacterium tuberculosis*.

Mycobacterial infections are notoriously difficult to treat. The organisms are hardy due to their cell wall, which is neither truly Gram negative nor Gram positive. In addition, mycobacteria are naturally resistant to various antibiotics that disrupt cell-wall biosynthesis, such as penicillin. Due to their unique cell wall, they can survive long exposure to acids, alkalis, detergents, oxidative bursts, lysis by complement, and many antibiotics. Most mycobacteria are susceptible to the antibiotics clarithromycin and rifamycin, but antibiotic-resistant strains have emerged.

Mycobacteria can be classified into several major groups for purpose of diagnosis and treatment: *Mycobacterium tuberculosis* complex, which can cause tuberculosis (*M. tuberculosis, M. bovis, M. africanum*, and *M. microti*); *Mycobacterium leprae*, which causes Hansen's disease or leprosy; and non-tuberculous mycobacteria (NTM), which can cause pulmonary disease resembling tuberculosis, lymphadenitis, skin disease, or disseminated disease.

The R-iminophenazine derivative clofazimine or CFZ ([3-(4-chloroanilino)-10-(4-chlorophenyl)-2,10-dihydro-2-(isopropylimino)-phenazine]; FIG. 1) was synthesized more than 50 years ago and found to be a strong antimycobacterial antibiotic (Barry, et al., 1957, Nature 179:1013-1015; O'Connor, et al., 1995, Drug Metab. Rev. 27:591-614; Reddy, et al., 1999, J. Antimicrob. Chemother. 43:615-623). Although able to kill most mycobacteria in vitro including *Mycobacterium tuberculosis*, CFZ was ineffective in animal models of tuberculosis (Barry, et al., 1957, Nature 179:1013-1015; O'Connor, et al., 1995, Drug Metab. Rev. 27:591-614; Reddy, et al., 1999, J. Antimicrob. Chemother. 43:615-623). CFZ achieved status as an antibiotic in the treatment of leprosy and is currently part of the three-drug treatment regimen approved for multibacillary disease by the World Health Organization (Reddy, et al., 1999, J. Antimicrob. Chemother. 43:615-623).

The apparent inability of most mycobacteria, including isolates of *Mycobacterium tuberculosis*, to develop resistance to CFZ (Reddy, et al., 1999, J. Antimicrob. Chemother. 43:615-623) has led to a resurgence of interest in the drug. Currently, new CFZ analogs are being tested for treatment of *Mycobacterium avium* infections associated with AIDS and for multi-drug resistant tuberculosis (Reddy, et al., 1999, J. Antimicrob. Chemother. 43:615-623; Reddy, et al., 1996, Antimicrob. Agents Chemother. 40:633-636; Sano, et al., 2004, Antimicrob. Agents Chemother. 48:2132-2139; and Van Rensburg, et al., 2000, Chemother. 46:43-48). Although CFZ has primarily antimycobacterial activity, experimental evidence suggests a broader based activity toward Gram-positive bacteria (Oliva, et al., 2004, J. Antimicrob. Chemother. 53:435-440; Van Rensburg, et al., 1992, Antimicrob. Agents Chemother. 36:2729-2735) and strains of yeast (Rhodes, et al., 1973, Biochem. Pharmacol. 22:1047-1056). Apart from its antibiotic properties, CFZ appears to have anti-inflammatory properties exhibiting the ability to suppress neutrophil and lymphocyte activity (Krajewska, et al., 1993, Int. J. Immunopharmac. 15:99-111; Zeis, et al., 1986, Int. J. Immunopharmac. 8:731-739; Sanchez, et al., 2000, Clin. Dermatol. 18:131-145; Ren, et al., 2008, PLoS ONE 3:1-11). This immunosuppressive effect currently is being explored in treatments of autoimmune disorders, including multiple sclerosis, lupus, and psoriasis (Sanchez, et al., 2000, Clin. Dermatol. 18:131-145; Ren, et al., 2008, PLoS ONE 3:1-11). Lastly, CFZ may have anticancer activity (Van Rensburg, et al., 1993, Cancer Res. 53:318-323; Durandt, et al., 2001, Int. J. Oncol. 19:579-583).

The mechanism(s) of action of CFZ has remained elusive. The drug is extremely hydrophobic (c Log P=7.5), suggesting that it functions in association with membranes (O'Connor, et al., 1995, Drug Metab. Rev. 27:591-614: Franzblau, et al., 1989, Antimicrob. Agents Chemother. 33:2004-2005). Studies have pointed to inhibition of $K^+$ transport, but it is not clear whether inhibition results from a specific interaction(s) or is a consequence of membrane disruption (Bopape, et al., 2004, J. Antimicrob. Chemother. 53:971-974; Cholo, et al., 2006, J. Antimicrob. Chemother. 57:79-84). CFZ also is reported to bind to DNA, but the mechanism of this interaction is unclear and does not appear to be through base intercalation like other dyes that disrupt DNA function (Morrison, et al., 1976, Int. J. Lepr. 44:475-481).

The first published study on CFZ noted that it was a redox active compound and that it was reduced and oxidized within mycobacteria, likely in conjunction with respiratory chain activity (Barry, et al., 1957, Nature 179:1013-1015). Because reduced forms of dyes such as CFZ were known to produce reactive oxygen species (ROS) upon reoxidation in air, it was argued that the generation of ROS was an important aspect of the mechanism of action of the drug. In support of this argument, mycobacteria deficient in catalase activity showed a greater sensitivity to CFZ than wild type bacteria.

There is a need in the art to identify novel compounds useful in the treatment of mycobacterial infections. These compounds should be active against mycobacteria and highly developable as drugs. There is further a need for novel agents that are active against Gram-positive bacteria or yeast. There is also a need for novel anti-inflammatory agents. Such agents may be useful in treating autoimmune disorders, including for example multiple sclerosis, lupus, and psoriasis. There is further a need for novel anticancer agents. The present invention addresses these needs.

BRIEF SUMMARY OF THE INVENTION

The invention includes a composition comprising a compound of formula (I), or a salt or solvate thereof:

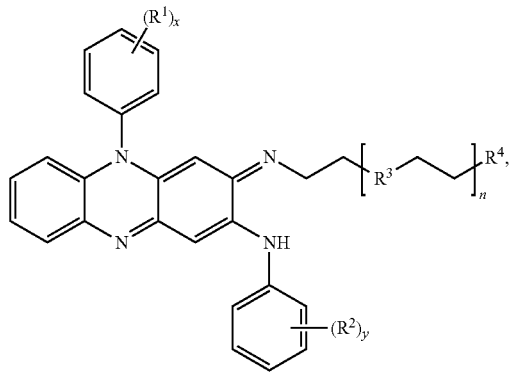

(I)

wherein:
each occurrence of $R^1$ and $R^2$ is independently selected from the group consisting of F, Cl, Br, I, CN, $NO_2$, $OR^5$, $SR^5$, $S(=O)R^6$, $S(=O)_2R^6$, $NHS(=O)_2R^6$, $C(=O)R^5$, $OC(=O)R^5$, $CO_2R^5$, $OCO_2R^6$, $N(R^5)_2$, $C(=O)N(R^5)_2$, $OC(=O)N(R^5)_2$, $NHC(=O)NH(R^5)$, $NHC(=O)R^5$, $NHC(=O)OR^5$, $C_1$-$C_6$ alkyl, $C_1$-$C_6$ fluoroalkyl and $C_1$-$C_6$ heteroalkyl;
each occurrence of $R^3$ is independently selected from the group consisting of $N(R^5)$, $CH_2N(R^5)$, O, and $CH_2O$;
$R^4$ is selected from the group consisting of $(CH_2)_mOR^5$, $(CH_2)_mN(R^5)_2$, and $(CH_2)_mNR^5C(C=N^5)N(R^5)_2$;
each occurrence of $R^5$ is independently selected from the group consisting of H, $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);
each occurrence of $R^6$ is independently selected from the group consisting of $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);
each occurrence of x and y is independently selected from the group consisting of 0, 1, 2, and 3;
n is an integer ranging from 0 to 4; and
m is an integer ranging from 0 to 3.

In one embodiment, each occurrence of $R^1$ and $R^2$ is independently selected from the group consisting of F, Cl, Br, I, CN, $NO_2$, COOH, $C(=O)NH_2$ and $C(=O)NH$—$C_1$-$C_6$ alkyl. In another embodiment, $R^4$ is selected from the group consisting of OH, $NH_2$, $NHC(C=H)NH_2$ and $(CH_2)_2NHC(C=H)NH_2$. In yet another embodiment, each occurrence of $R^3$ is independently selected from the group consisting of N(H), $CH_2N(H)$, O, and $CH_2O$.

In one embodiment, the compound of formula (I) is selected from the group consisting of: (Z)-3-((2-(2-(2-aminoethoxy)ethoxy)ethyl)imino)-N,5-bis(4-chlorophenyl)-3,5-dihydrophenazin-2-amine; (Z)—$N^1$-(2-aminoethyl)-$N^2$-(2-((10-(4-chlorophenyl)-3-((4-chlorophenyl)amino)phenazin-2(10H)-ylidene)amino)ethyl) ethane-1,2-diamine; (Z)—$N^1$-(2-aminoethyl)-$N^2$-(2-((10-(phenyl)-3-((phenyl)amino)phenazin-2(10H)-ylidene)amino)ethyl)ethane-1,2-diamine; (Z)-1-(2-((10-(4-chlorophenyl)-3-((4-chlorophenyl)amino) phenazin-2(10H)-ylidene)amino)ethyl) guanidine; (Z)-1-(2-((10-(phenyl)-3-((phenyl)amino)phenazin-2(10H)-ylidene) amino)ethyl)guanidine; (Z)—$N^1$-(3-((10-phenyl-3-(phenylamino)phenazin-2(10H)-ylidene)amino)propyl) butane-1,4-diamine; (Z)-1-(4-((3-((10-phenyl-3-(phenylamino) phenazin-2(10H)-ylidene)amino)propyl) amino)butyl)guanidine; (Z)-1-(2-(2-(2-((10-(4-chlorophenyl)-3-((4-chlorophenyl)amino) phenazin-2 (10H)-ylidene)amino)ethoxy) ethoxy)ethyl)guanidine; (Z)-1-(2-(2-(2-((10-(4-nitrophenyl)-3-((4-nitrophenyl)amino) phenazin-2(10H)-ylidene)amino)ethoxy) ethoxy)ethyl) guanidine; (Z)-1-(2-(2-(2-((10-(phenyl)-3-((phenyl)amino) phenazin-2(10H)-ylidene)amino)ethoxy)ethoxy)ethyl) guanidine; (Z)-1-(2-(2-(2-((10-(4-carboxyphenyl)-3-((4-carboxyphenyl)amino) phenazin-2(10H)-ylidene)amino) ethoxy)ethoxy)ethyl)guanidine; (Z)-1-(2-(2-(2-((10-(4-hydroxyphenyl)-3-((4-hydroxyphenyl)amino)phenazin-2 (10H)-ylidene)amino) ethoxy)ethoxy)ethyl) guanidine; (Z)-1-(2-(2-(2-((10-(4-carbamoylphenyl)-3-((4-carbamoylphenyl)amino) phenazin-2(10H)-ylidene)amino) ethoxy)ethoxy)ethyl)guanidine; (Z)-1-(2-((10-(4-nitrophenyl)-3-((4-nitrophenyl)amino)phenazin-2(10H)-ylidene)amino)ethyl) guanidine; (Z)-1-(2-((10-(4-carboxyphenyl)-3-((4-carboxyphenyl)amino)phenazin-2 (10H)-ylidene)amino)ethyl)guanidine; (Z)-1-(2-((10-(4-carbamoylphenyl)-3-((4-carbamoylphenyl)amino)phenazin-2(10H)-ylidene)amino)ethyl)guanidine; (Z)-1-(2-((10-(4-(N-methyl)carbamoylphenyl)-3-((4-(N-methyl) carbamoylphenyl)amino) phenazin-2(10H)-ylidene)amino) ethyl) guanidine; (Z)-1-(2-((10-(4-hydroxyphenyl)-3-((4-hydroxyphenyl)amino)phenazin-2(10H)-ylidene)amino) ethyl)guanidine; a salt or solvate thereof, and any combinations thereof.

In one embodiment, the composition further comprises at least one pharmaceutically acceptable carrier.

The invention also includes a method of treating or preventing a *mycobacterium* infection in a subject in need thereof. The method comprises administering to the subject a therapeutically effective amount of a pharmaceutically acceptable composition comprising a compound of formula (I), or a salt or solvate thereof, whereby the *mycobacterium* infection in the subject is treated or prevented. In one embodiment, the *mycobacterium* comprises *M. smegmatis, M. tuberculosis, M. bovis, M. africanum, M. microti,* or *M. leprae.*

The invention further includes a method of treating or preventing a Gram-positive bacterium infection in a subject in need thereof. The method comprises administering to the subject a therapeutically effective amount of a pharmaceutically acceptable composition comprising a compound of formula (I), or a salt or solvate thereof, whereby the Gram-positive bacterium infection in the subject is treated or prevented.

The invention also includes a method of treating or preventing a yeast infection in a subject in need thereof. The method comprises administering to the subject a therapeutically effective amount of a pharmaceutically acceptable composition comprising a compound of formula (I), or a salt or solvate thereof, whereby the yeast infection in the subject is treated or prevented.

The invention further includes a method of treating or preventing an inflammatory condition in a subject in need thereof. The method comprises administering to the subject a therapeutically effective amount of a pharmaceutically acceptable composition comprising a compound of formula (I), or a salt or solvate thereof, whereby the inflammatory condition in the subject is treated or prevented.

The invention also includes a method of treating or preventing an auto-immune disorder in a subject in need thereof. The method comprises administering to the subject a therapeutically effective amount of a pharmaceutically acceptable composition comprising a compound of formula (I) or a salt or solvate thereof, whereby the auto-immune disorder in the subject is treated or prevented.

In one embodiment, the auto-immune disorder comprises multiple sclerosis, lupus, or psoriasis.

The invention further includes a method of treating or preventing a proliferative disease in a subject in need thereof. The method comprises administering to the subject a therapeutically effective amount of a pharmaceutically acceptable composition comprising a compound of formula (I) or a salt or solvate thereof, whereby the proliferative disease in the subject is treated or prevented. In one embodiment, the proliferative disease is cancer.

In one embodiment, the compound of formula (I), or a salt or solvate thereof, is:

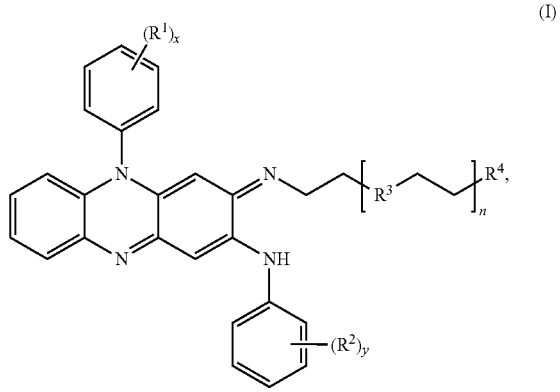

(I)

wherein:

each occurrence of $R^1$ and $R^2$ is independently selected from the group consisting of F, Cl, Br, I, CN, $NO_2$, $OR^5$, $SR^5$, $S(=O)R^6$, $S(=O)_2R^6$, $NHS(=O)_2R^6$, $C(=O)R^5$, $OC(=O)R^5$, $CO_2R^5$, $OCO_2R^6$, $N(R^5)_2$, $C(=O)N(R^5)_2$, $OC(=O)N(R^5)_2$, $NHC(=O)NH(R^5)$, $NHC(=O)R^5$, $NHC(=O)OR^5$, $C_1$-$C_6$ alkyl, $C_1$-$C_6$ fluoroalkyl and $C_1$-$C_6$ heteroalkyl;

each occurrence of $R^3$ is independently selected from the group consisting of $N(R^5)$, $CH_2N(R^5)$, O, and $CH_2O$;

$R^4$ is selected from the group consisting of $(CH_2)_mOR^5$, $(CH_2)_mN(R^5)_2$, and $(CH_2)_mNR^5C(C=N^5)N(R^5)_2$;

each occurrence of R is independently selected from the group consisting of H, $C_1$-$C_6$ alkyl. $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl. $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of $R^6$ is independently selected from the group consisting of $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of x and y is independently selected from the group consisting of 0, 1, 2 and 3;

n is an integer ranging from 0 to 4; and m is an integer ranging from 0 to 3.

In one embodiment, the subject is a mammal. In another embodiment, the mammal is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2, comprising FIGS. 2A-2B, is a set of graphs illustrating the effect of CFZ on NADH oxidation catalyzed by isolated *M. smegmatis* and *E. coli* membranes. FIG. 2A: NADH oxidation catalyzed by *M. smegmatis* membranes (Mem) was monitored at 340 nm in a cuvette. Reactions were performed in total volume of 250 μl containing 10.0 μg membrane protein, 250 μM NADH with 20 mM KCN and CFZ added as indicated. Breaks in the trace indicate additions to the reaction; the amounts of CFZ reported are cumulative values. Dashed line indicates "control" activity measured in the absence of KCN and CFZ. The sharp absorbance increases at ≥4.7 μg/ml CFZ are due in part to CFZ absorbance and possibly to light scattering upon saturation of membranes with CFZ. FIG. 2B: NADH oxidation by *E. coli* membranes was measured similarly. Reaction conditions were the same, except membrane protein added was 4.0 μg membrane protein and KCN concentration was 5.0 mM.

FIGS. 3A-3B, is a series of graphs illustrating the ability of CFZ (FIG. 3A) or KS6 (FIG. 3B) to restore NADH oxidase activity in isolated *M. smegmatis* membrane preparations treated with KCN. FIG. 3A: NADH oxidase activity as a function of the amount of CFZ added to reactions was determined from time courses performed as in FIG. 2. Oxidation rates were determined from the slopes of the lines associated with the various additions. Fraction activity restored is the ratio of the NADH oxidation rates produced by CFZ addition to membrane preparations after KCN addition as in FIG. 2, divided by the NADH oxidation rate before the addition of KCN. All rates were measured as $\Delta A_{340}$ nm/min. The rate at 0.0 CFZ is the fractional activity remaining after KCN addition. Sets 1 and 2 refer to membrane preparations in two time-separated studies (approximately 1 year apart). The amount of membrane added to reactions was standardized to have an activity in the range of 0.1 A/min at 340 nm; the measured control NADH oxidase rates averaged 0.130±0.5 (n=13) for log membranes and 0.114±0.04 (n=15) for stationary membranes. Standardized to protein, stationary phase membranes had less activity than log phase membrane; thus, to achieve similar activities, log phase reactions contained an average of 3.8±1.6 μg membrane protein, and stationary phase reactions contained an average of 13.0±5.5 μg membrane protein. FIG. 3B: experimental conditions were similar to those in FIG. 3A, except that KS6 was added to reactions instead of CFZ. Data are the average and S.D. of three measurements. In the case of set 2 membranes, membrane preparations from the three separate log phase growths were each assayed once, and the results were averaged, and membrane preparations from the three stationary phase growths were each assayed once, and the results were averaged. In the case of set 1, only stationary stage membranes were assayed, two different membrane preparations were assayed separately, and the results were averaged; the data reported are the average values, and the error bars are the deviation from the average. The molecular weight of KS6 was greater than that of CFZ (562 versus 473 Da), which accounts for the difference in x axis values in the two panels.

FIG. 6, comprising FIG. 6A: time course showing reduction (absorbance decrease) and spontaneous oxidation of CFZ. Reaction conditions were similar to those in FIG. 5, except that absorbance was monitored continuously at a single wavelength of 470 nm. Breaks in the trace are due to raising/closing the door of the spectrophotometer to make additions. The order of addition to the 250-µl reaction were (1) membranes (40 µg membrane protein) and 2.4 µg CFZ, (2) 20 mM KCN, (3) 225 µM NADH, (4) second addition of 225 µM NADH after return of absorbance, and (5) manual agitation of the reaction by vigorous shaking of the cuvette. FIG. 6B: the reactions was performed similar to FIG. 6A, except that the NADH and CFZ concentrations were increased. The order of addition to the 250 µl reaction were (1) membranes (Memb, 85 µg membrane protein) and 6.0 µg CFZ, (2) 20 mM KCN, (3) 500 µM NADH, and (4) agitation of the cuvette. FIG. 6C: same as FIG. 6B, except for the addition of SDS during the slow phase of absorbance loss. Additions to reaction were (1) membranes, KCN, and CFZ as in FIG. 6B, (2) 225 µM NADH, (3) SDS (0.4% final) with agitation, and (4) second addition of NADH.

FIG. 7, comprising FIGS. 7A-7B, is a series of graphs illustrating ROS production catalyzed by *M. smegmatis* log-phase membranes in the absence and presence of CFZ. FIG. 7A: demonstration of CFZ-mediated ROS production. NADH oxidation and ROS production were measured in separate reactions following absorbance at either 340 nm (right axis, dashed line) or 563 nm (left axis, solid lines), respectively. Reactions were preformed in 1.0 ml containing 20 µg membrane protein, either NADH (0.2 mM) or succinate (1.0 mM) as electron donors, CFZ (0.5 µg) or TPZ (0.2 mM), and ROS detection reagents. FIG. 7B: dependence of ROS production on the amount of CFZ. This study was performed in 50 µl total volume using a plate reader (Tecan Corp.). The reaction contained 1.0 µg of log-phase membranes and different amounts of CFZ as indicated in the panel. Parallel reactions were monitored at 340 nm and 563 nm. At each concentration, initial velocities for the rate of NADH consumption and resorufin production were used to calculate flux of electrons producing resorufin relative to NADH oxidation rate (y axis).

FIG. 8, comprising FIG. 8A-8B, is a series of graphs illustrating reduction of CFZ (FIG. 8A) and ROS production (FIG. 8B) catalyzed by purified recombinant *M. tuberculosis* NDH-2. FIG. 8A: spectra showing reduction of CFZ by NDH-2 under anaerobic conditions and subsequent reoxidation. Stock CFZ in $Me_2SO$ was added to a solution of 50 mM MOPS/Na+, pH 6.5, 2.0 mM $MgCl_2$ to produce a final concentration of 1.18 µg/ml. Based on spectra taken during a 40-min period (CFZ in buffer), ~70% of the CFZ remained in solution exhibiting a spectrum consistent with cationic CFZ. NADH (200 µM) was then added; it did not produce a significant change during a 10-min incubation period (+NADH). Purified NDH-2 (2.7 µg/ml, 0.01% Big CHAPS at final) was then added to start the reaction (1 min), and additional spectra were taken at the indicated times. After the absorbance loss was complete, the cuvette was exposed to air for 20 min after which a spectrum was recorded (air-oxidized). FIG. 8B: production of ROS by purified NDH-2. NADH oxidation (340 nm absorbance decrease) and ROS generation (absorbance increase, 563 nm) catalyzed by NDH-2 was measured under aerobic conditions similar to the reactions in FIG. 7. Reactions were performed in a total volume of 1.0 ml and contained 200 µM NADH with an ROS detection system. At the indicated times, NDH-2 was added to final concentration of 2.0 µg/ml, followed by CFZ to a final of 1.0 µg/ml or TPZ to a final of 200 µM.

FIGS. 9A-9B, is a series of graphs illustrating CFZ-mediated (FIG. 9A) and KS6-mediated (FIG. 9B) restoration of NADH oxidation by membranes isolated from non-mycobacterial organisms. Measurements and data reported were made as described in FIGS. 2 and 3. Bacterial membranes in the assays had a starting NADH oxidase activity of ~0.1 ΔA/min at 340 nm/min. The mitochondrial preparations had an activity of 0.05 ΔA/min at 340 nm.

FIG. 10, comprising FIGS. 10A-10B, illustrates inhibition of *M. smegmatis* growth by CFZ and INH and effect of antioxidants. FIG. 10A: effect of CFZ on colony counts of wild type *M. smegmatis* $mc_2$ 155 plated on 7H9 agar. Data at each concentration represent the average colony number on three plates±S.D. FIG. 10B: effect of free radical scavengers on CFZ inhibition of *M. smegmatis* growth. *M. smegmatis* was grown on agar plates containing various antioxidants (5.0 mM 4-hydroxy-TEMPO, 5.0 mM N-acetylcysteine (NAC), and 12.5 µg/ml α-tocopherol) with or without 0.5 µg/ml CFZ or 10 µg/ml INH. Representative plates demonstrating bacterial growth under the various conditions are shown.

FIG. 12, comprising FIG. 12A: Spectra of CFZ remaining in solution after centrifugation. Five μL of stock CFZ (5.0 mM in $Me_2SO$) was diluted with 0.5 mL buffer to produce the equivalent of a 50 μM solution. The solutions were incubated overnight at 23° C. and then centrifuged in an AEC centrifuge at 15K rpm (21,000×g) for 2 min. The supernatant was removed and centrifuged a second time. After the second centrifugation, supernatants were removed and spectra were obtained. FIG. 12B: Spectra of pelleted CFZ dissolved in EtOH/CAPs. Pellets from centrifugations were dissolved in 1.0 mL EtOH containing 50 μL of 0.5 M CAPS and spectra recorded. Appropriate solvent backgrounds were subtracted from all spectra.

FIG. 13, comprising FIGS. 13A-13C, is a series of graphs illustrating solubility of 50 μM CFZ in a neutral and anionic detergent. FIG. 13A: Spectra of CFZ in 1.0% Triton X-100 (w/v) adjusted to various pH with buffers as described in FIG. 12. FIG. 13B: Spectra of CFZ in 1.0% Na-lauroylsarcosine (w/v) adjusted to pH with buffers. Solutions were incubated for at least 2 hr and supernatants were removed to obtain spectra; no precipitated material was observed with either detergent. FIG. 13C: The pH dependency determining the proportion of cationic and uncharged CFZ species in TX-100.

FIG. 14, comprising FIG. 14A: Spectra (buffer background subtracted) of membranes (60 μg/0.5 mL incubation) suspended in 0.1 M HEPES pH 7.0 to which increasing amounts of CFZ were added. Amounts added to incubation were 1.2, 2.4, 4.8, 7.2, 9.6, 12, and 14.4 μg. FIG. 14B: Spectra of 2.5 μg CFZ in 250 μL of 0.1 M HEPES pH 7.0 to which increasing amounts of membrane were added. Vertical hashed lines mark absorbance at 452 and 492 nm.

FIG. 15 is a scheme illustrating the synthesis of KS6.

FIG. 17, comprising FIG. 17A: spectra were determined after centrifugation as described in FIG. 12. The amount of KS6 added was equivalent to 50 μM. FIG. 17B: spectra were obtained after centrifugation and transition spectra were obtained at pH 6.0, 6.5, 7.0, and 7.5.

FIG. 18 is a graph illustrating redox cycling of KS6. Additions to a cuvette containing 250 μL of 0.1 M HEPES pH 7.0 were: KS6 (7 μg), M. smegmatis membranes (14 μg protein), NADH 225 μM, NADH 225 μM. Agitation was achieved by removing the cuvette from the spectrophotometer and shaking vigorously.

FIG. 19, comprising FIGS. 19A-19C, illustrates non-limiting examples of compounds of the invention.

FIG. 20, comprising

FIG. 21, comprising FIG. 21A: NADH-Q0 reductase activity of E. faecalis membranes. The reaction contained 0.2 mM NADH and E. faecalis membrane, and 50 μM Q0 was subsequently added to the reaction at each addition. NADH-Q0 reduction was stoichiometric. FIG. 21B: Effect of NDH-2 inhibitor, chlorpromazin (CPZ), on the E. faecalis NADH-Q0 reductase activity. NADH oxidation by membranes in the presence of 0.2 mM NADH and 2 mM Q0, completely ceased on addition of 400 μM CPZ. FIG. 21C: ROS production by E. faecalis membranes in the presence of NADH and KS6. ROS production was monitored at 563 nm using the AmplexRed assay (see Biochemical Mechanism of action). The reaction was initiated by adding 50 μM NADH. The concentration of DMSO was the same in the control and the reactions containing KS6 and/or CPZ.

DETAILED DESCRIPTION OF THE INVENTION

Figure 1:
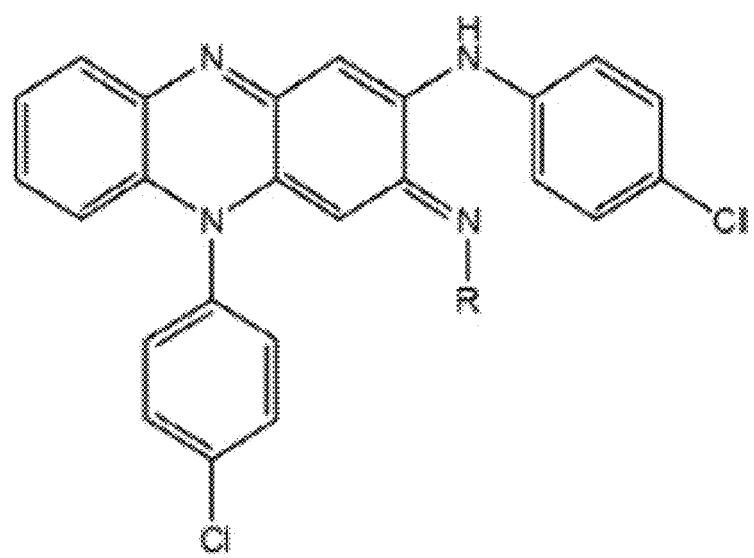
FIG. 1 illustrates the structure of clofazimine (CFZ).

The present invention relates to the unexpected discovery of novel derivatives of clofazimine, which are more soluble and developable than clorazimine itself. In one aspect, the compounds of the invention are useful in treating infections by mycobacteria, such as but not limited to M. smegmatis and M. tuberculosis. In another aspect, the compounds of the invention are useful in treating infections by Gram-positive bacteria or yeast. In yet another aspect, the compounds of the invention are useful in treating inflammatory conditions. In yet another aspect, the compounds of the invention are useful in treating autoimmune disorders, including for example multiple sclerosis, lupus, or psoriasis. In yet another aspect, the compounds of the invention are useful in treating proliferative diseases, such as cancer.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "CFZ" refers to clofazimine([3-(4-chloroanilino)-10-(4-chlorophenyl)-2,10-dihydro-2-(isopropylimino)-phenazine]) or a salt thereof.

As used herein, the term "INH" refers to isoniazid or a salt thereof.

As used herein, the term "NDH-2" refers to NADH-quinone oxidoreductase type 2 or a salt thereof.

As used herein, the term "TPZ" refers to trifluoperazine or a salt thereof.

As used herein, the term "TEMPO" refers to 2.2',6,6'-tetramethyl-piperidinyl-1-oxy or a salt thereof.

As used herein, the term "KS6" refers to 3-(4-chloroanilino)-10-(4-chlorophenyl)-2-[4-(8-amino-3,6-dioxaoctyl)]imino]-2,10-dihydrophenazine or a salt thereof.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics. In one embodiment, the condition is selected from a *mycobacterium* infection, a Gram-positive bacterium infection, an yeast infection, an inflammatory condition, an auto-immune disorder, a proliferative disease, and a combination thereof.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-tolunenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

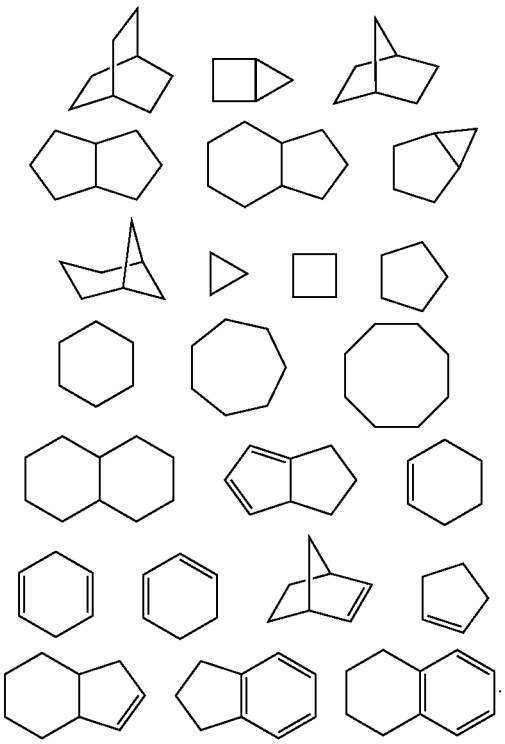

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

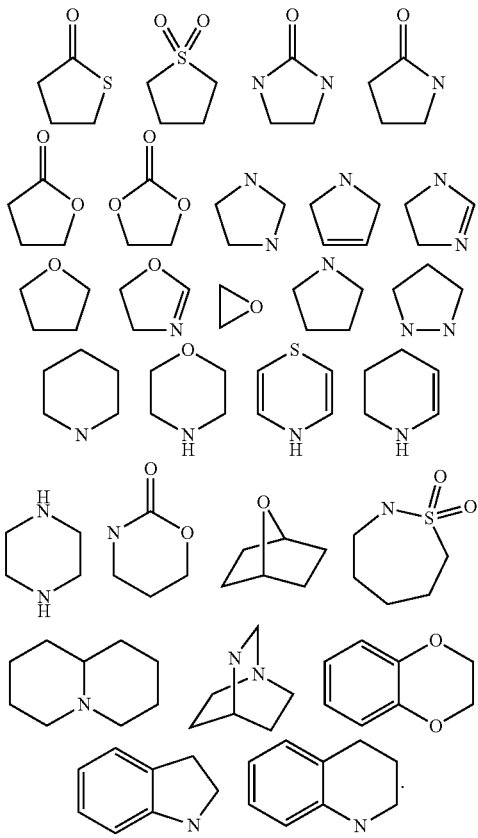

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group. e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

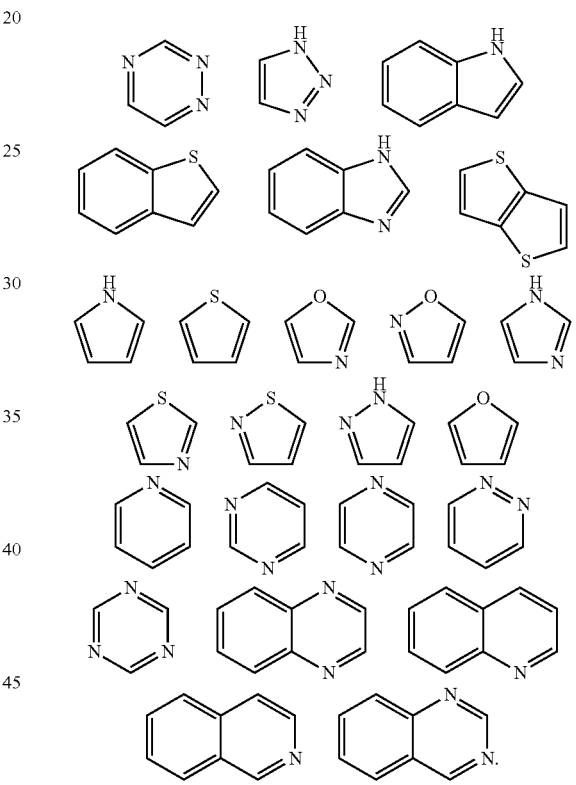

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(═O)$_2$alkyl, —C(═O)NH[substituted or unsubstituted alkyl, or substituted or unsubstituted phenyl], —C(═O)N[H or alkyl]$_2$, —OC(═O)N[substituted or unsubstituted alkyl]$_2$, —NHC(═O)NH [substituted or unsubstituted alkyl, or substituted or unsubstituted phenyl], —NHC(═O)alkyl, —N[substituted or unsubstituted alkyl]C(═O)[substituted or unsubstituted alkyl], —NHC(═O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(═O)$_2$—CH$_3$, —C(═O)NH$_2$, —C(═O)—NHCH$_3$, —NHC(═O)NHCH$_3$, —C(═O)CH$_3$, and —C(═O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

As used herein, the term "container" includes any receptacle for holding the pharmaceutical composition. For example, in one embodiment, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing HBV infection in a patient.

"Instructional material," as that term is used herein, includes a publication, a recording, a diagram, or any other medium of expression that may be used to communicate the usefulness of the compounds and/or methods of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

DESCRIPTION

Figure 11:
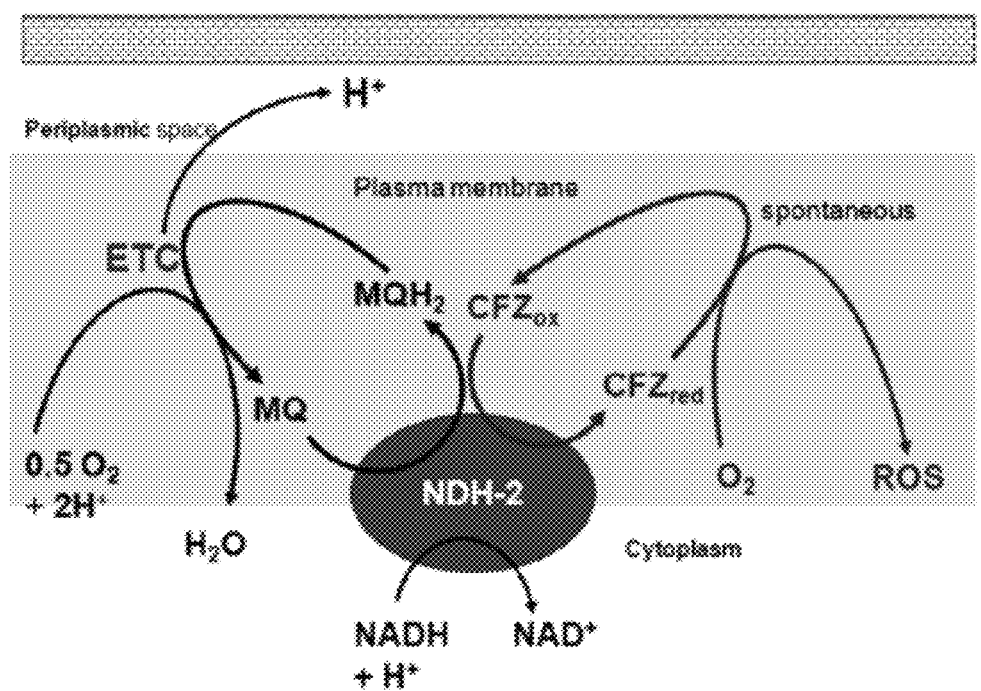
FIG. 11 is a scheme illustrating a depiction of CFZ-mediated redox cycling and ROS production. The diagram depicts menaquinone (MQ) of the respiratory chain and CFZ as competing substrates of NDH-2. The electron transport chain (ETC) in *M. smegmatis* is primarily composed of two oxidoreductases in addition to NDH-2: cytochrome $bc_1$ complex, which is reduced by menaquinol, and cytochrome $aa_3$, which obtains electrons from cytochrome bc1 and transfers them to $O_2$ in a coupled reaction that produces water and the translocation of protons from the cytoplasm to periplasmic space. Oxidation of reduced CFZ by oxygen occurs nonenzymatically and produces ROS. The cell wall of M. smegmatis is much thicker than depicted in the diagram.

The studies reported herein indicate a pathway in *M. smegmatis* for ROS generation coupled to the redox cycling of CFZ (FIG. 11). Although very sparingly soluble in water at pH 7.0, CFZ concentrates in membranes and this association stabilizes to a significant extent the cationic (protonated) form of the drug, which is reported to be the redox active form (Kovacic, et al., 1989, Bioelectrochem and Bioenerg. 21:269-278). Addition of CFZ to cyanide-inhibited membranes restored a significant fraction of the NADH oxidase activity. Restoration was shown to involve reduction of CFZ catalyzed by the respiratory oxidoreductase NDH-2. This reaction resulted in the direct transfer of electrons/H$^+$ from NADH to CFZ. Reduced CFZ was unstable and spontaneously reacted with O$_2$. A rough estimate suggests that the second order rate constant for this reaction was in the range of 100 M$^{-1}$ s$^{-1}$. CFZ-mediated NADH oxidation by membranes in the absence of KCN produced ROS as demonstrated using a coupled assay system to detect ROS. Taken together, the above results indicated that CFZ treatment of mycobacteria resulted in the generation of a cyclical pathway to produce ROS that is fueled by NADH and O$_2$ (FIG. 11). This cycle continually runs because NADH is a key substrate in generating ATP and is continually produced by the citric acid cycle and/or β-oxidation of fatty acids. On the other hand, the rate of the cycle could vary depending on the O$_2$ tension in various lung microenvironments where *M. tuberculosis* exists in tuberculosis.

NDH-2 is a membrane bound protein of ~50 kDa containing a single FAD moiety. It typically catalyzes the transfer of electrons from NADH to menaquinone, the only quinone type in mycobacteria, thereby contributing to respiratory chain activity in mycobacteria. Menaquinol continues the transfer by supplying electrons/H$^+$ to downstream respiratory chain oxidoreductases, which in turn use the electrons/H$^+$ to reduce O$_2$. The catalytic reduction of CFZ by NDH-2 and generation of ROS was confirmed using purified recombinant *M. tuberculosis* NDH-2. Succinate dehydrogenase, a citric acid cycle oxidoreductase, also transfers electrons to menaquinone upon oxidation of succinate to fumarate. Because succinate dehydrogenase could not drive CFZ reduction, it appears that NDH-2 is the only respiratory chain oxidoreductase capable of reducing CFZ. CFZ appears to compete with menaquinone for electrons carried by the FAD moiety of reduced NDH-2, although such competition was not documented in the present study. The catalytic reduction of CFZ by NDH-2 is the first demonstration of a specific interaction between CFZ and a bacterial constituent.

To produce cell death, ROS generation must increase to a level that overcomes detoxifying pathways (Keyer, et al., 1996 Proc. Nat. Acad. Sci. 93:13635-13640; and Raha, et al., 2000, Trends Biochem. Sci. 25:502-508). Experimental evidence suggests intracellular hydrogen peroxide levels need to be in the range of 1.0 mM for ROS to be cytotoxic/bactericidal (Keyer, et al., 1996, Proc. Nat. Acad. Sci. 93:13635-13640; Rosner, et al., 1994, Antimicrob. Agents Chemother. 38:1829-1833; and Kohanski, et al., 2007, Cell 130:797-810). Such levels apparently are obtained by treatment of cells/bacteria with naphthoquinones (e.g., plumbagin and menadione) which are routinely used to place cells and bacteria under oxidative stress (Inbaraj, et al., 2004, Chem. Res. Toxicol. 17:55-62; and Castro, et al., 2008, PLoS ONE 3 e3999). Naphthoquinones are well established redox cycling agents, with reduction/oxidation mediated by a quinone-like structural element. They are reduced by a number of enzymes, including soluble NADPH:cytochrome P450 reductases found in the cytoplasm of most cells, and complex 1, the mitochondrial NADH:quinone oxidoreduction referred to as NDH-1. Like CFZ, reduced forms of naphthoquinones are nonenzymatically oxidized by molecular $O_2$ to produce ROS.

Although described as quinoid-like (Kovacic, et al., 1989, Bioelectrochem and Bioenerg. 21:269-278), CFZ differs markedly in structure from naphthoquinones. It has no oxygen substituents and reduction likely involves nitrogen groups on the phenazine three-member ring in conjunction with a single imino group substituent. CFZ does not appear to be as toxic as naphthoquinones quite possibly because structural differences with more classical quinones limits reduction to specific enzymes such as NDH-2. Mitochondria and bacteria that predominantly express respiratory chain NADH:quinone oxidoreductases of the type I variety do not reduce CFZ. Moreover, the administration of CFZ to humans for treatment of leprosy and other disorders does not in general produce dramatic side effects other than skin discoloration (O'Connor, et al., 1995, Drug Metab. Rev. 27:591-614; Reddy, et al., 1999, J. Antimicrob. Chemother. 43:615-623; and Sanchez, et al., 2000, Clin. Dermatol. 18:131-145).

Figure 3:
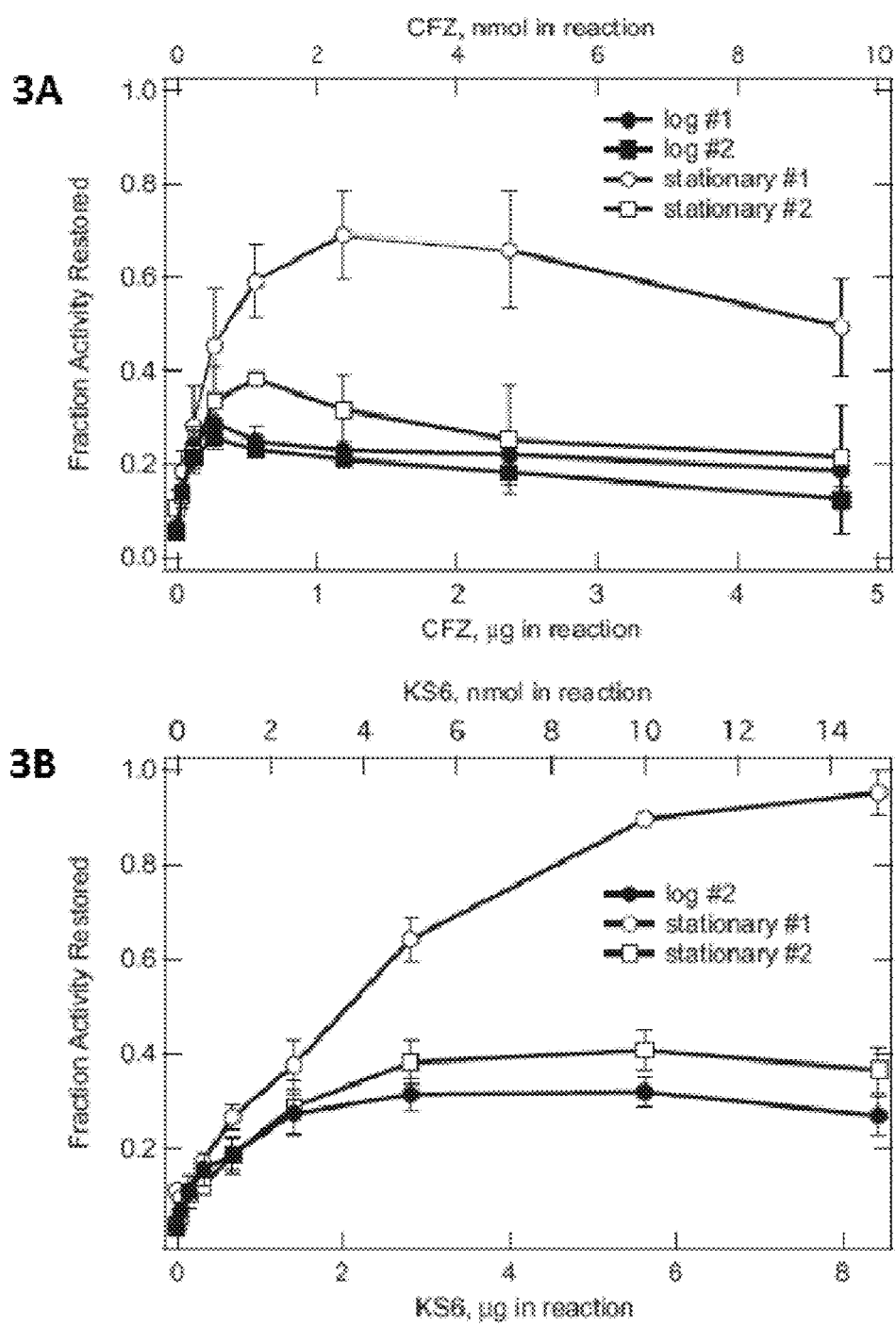
FIG. 3, comprising

Although CFZ is a more selective substrate than naphthoquinones, the coupling of ROS generation to a respiratory chain oxidoreductase may provide the high levels of intracellular ROS needed to affect bacterial growth. At least in *M. smegmatis* and *M. tuberculosis*, NDH-2 is the only oxidoreductase mediating the transfer of NADH electrons/$H^+$ to the respiratory chain (Weinstein, et al., 2005, Proc. Nat. Acad. Sci. U.S.A. 102:4548-4553; and Teh, et al., 2007, Inf. Disord. Drug Targets 7:169-181); thus, the entire respiratory chain flux from NADH is dependent on this oxidoreductase. Studies with KCN-treated membranes showed that CFZ-mediated NADH oxidase rates in membrane preparations were relatively fast attaining 25-70% of the oxidation rate measured in the absence of KCN with saturating NADH (FIG. 3A). Under the conditions where electron flow in the respiratory chain of membranes was not inhibited by KCN addition, CFZ-mediated ROS production attained a rate that was ~18% of the rate of the electron transport chain with near saturating NADH.

Strong support for a mechanism of action involving ROS was obtained in studies measuring bacterial growth. Colony formation on agar containing 0.5 µg/ml CFZ was undetectable. This apparent bactericidal activity was prevented by the addition of antioxidants to the medium. Three structurally different antioxidants, α-tocopherol, N-hydroxy-TEMPO, and N-acetylcysteine nullified the growth inhibitory activity of CFZ. Furthermore, their effect was specific for CFZ as INH inhibition of *M. smegmatis* growth was not altered by the same antioxidants. INH-mediated growth inhibition is primarily based on inhibition of mycolic acid synthesis (Rosner, et al., 1994, Antimicrob. Agents Chemother. 38:1829-1833; and Timmins, et al., 2006, Mol. Microbiol. 62:1220-1227). The activation of INH in mycobacteria is believed to be mediated by catalase activity, implying a requirement for peroxides (Rosner, et al., 1994, Antimicrob. Agents Chemother. 38:1829-1833; and Timmins, et al., 2006, Mol. Microbiol. 62:1220-1227). Because antioxidants should reduce cellular peroxide levels, the lack of an effect on INH inhibition is unclear. Although lower in the presence of antioxidants, the peroxide level might have been still sufficient to activate INH by catalase. In contrast, the same low cellular ROS level was probably not adequate to be bactericidal.

CFZ affects a spectrum of Gram-positive but not Gram-negative bacteria (Van Rensburg, et al., 1992, Antimicrob. Agents Chemother. 36:2729-2735). Gram-positive species reported sensitive to CFZ other than mycobacteria include *Staphylococcus, Streptococcus, Enterococcus*, and *Listeria*. Although limited in extent, the study characterizing the interaction of CFZ with *S. aureus* membranes suggested a response to the drug somewhat different than observed for *M. smegmatis*. CFZ addition to *S. aureus* membranes inhibited by KCN addition demonstrated a return of NADH oxidase activity (FIG. 10). However, restoration of this activity became rapidly inhibited as the CFZ dose increased. A parallel study with KS6, a more soluble form of CFZ, did not show the inhibitory activity, suggesting that the binding of CFZ to *S. aureus* membranes may be more structurally disruptive than to *M. smegmatis* membranes.

CFZ may have more than one mechanism of action due to its lipophilic nature and preference to accumulate in membranes. Stabilization of cationic CFZ, presumably by negatively charged membrane lipids could be particularly disruptive to membrane integrity (Yang, et al., 2007. J. Am. Chem. Soc. 129:12141-12147; Epand, et al., 2007, Biochem. Biophys. ACTA 1768:2500-2509; Epand, et al., 2008, J. Am. Chem. Soc. 130:14346-14352; and Lai, et al., 2008, Ace. Chem. Res. 41:1233-1240). Such disruption could affect embrane functions such as $K^+$ transport. The interaction of CFZ with DNA probably also reflects the hydrophobicity of the drug. However, it is unclear why mechanisms of action based on binding to membranes or DNA should be limited to Gram-positive bacteria. Low levels of CFZ inhibit ATP synthesis activity in isolated inverted bacterial membranes. The inhibition occurs substantially below the point of membrane saturation and might represent a second mechanism of action of a specific nature.

Gram-negative bacteria appear generally insensitive to CFZ (Van Rensburg, et al., 1992, Antimicrob. Agents Chemother. 36:2729-2735). As shown here, membranes isolated from three different Gram-negative bacteria, *E. coli, P. denitrificans*, and *P. aeruginosa* did not exhibit significant CFZ-mediated NADH oxidation or ROS production. They also did not react significantly with the more soluble CFZ analog KS6. Three NADH:quinone oxidoreductases that function in the respiratory chain of bacteria have been described: NDH-1, NDH-2, and a sodium pumping NDH (Yano, et al., 2001, J. Bioenerg. Biomembr., 33:213-222; and Melo, et al., 2004, Microbiol. Mol. Biol. Rev., 68:603-616). Mycobacteria are unusual in that only NDH-2 is functional. E. coli expresses NDH-1 and NDH-2 (Melo, et al., 2004, Microbiol. Mol. Biol. Rev. 68:603-616), and both were active in the preparations of isolated membranes. Based on the use of NDH-1 specific substrate, deamino-NADH, ~40% of the total membrane NADH oxidase activity was due to NDH-2. NDH-1 is the only functional NADH:quinone oxidoreductase associated with the respiratory chain of *P. denitrificans*, a bacterium used as a model system for mitochondrial respiration (John, et al., 1975, Nature 254:495-498; Yagi, et al., 1998, Biochem. Biophys. ACTA 1364:125-133; Baker, et al., 1998, Microbiol. Mol. Biol. Rev. 62:1046-1078) and *P. aeruginosa* expresses three oxidoreductases in undetermined proportion (Melo, et al., 2004, Microbiol. Mol. Biol. Rev. 68:603-616). The negative results with these bacteria indicate that NDH-1 does not interact with CFZ and that the ability to reduce CFZ is a property of some, but not all, NDH-2 oxidoreductases. The inability of rat mitochondria to reduce CFZ is consistent with the inability of NDH-1 to reduce CFZ.

Although membranes from the above Gram-negative bacteria could not generate ROS, membranes isolated from *S. aureus*, a Gram-positive bacteria and submitochondrial particles isolated from *S. cerevisiae* were able to oxidize NADH and generate ROS in the presence of CFZ. It might appear inconsistent for *S. cerevisiae*, a eukaryotic organism, to show sensitivity to CFZ; however, this yeast does not express NDH-1 but uses NDH-2 type oxidoreductases in the respiratory chain (de Vries, et al., 1988, Eur. J. Biochem. 176:377-384). The inspection of the *S. aureus* genome identified a gene coding for an NDH-2 type oxidoreductase, but no evidence for an operon encoding the numerous subunits composing NDH-1.

CFZ is active against multidrug-resistant strains of *M. tuberculosis* in vitro, and *M. tuberculosis* in general shows very little ability to develop resistance to the drug (Reddy, et al., 1999, J. Antimicrob. Chemother. 43:615-623). The need for new antibiotics to combat resistant strains has renewed interest CFZ and in the development of new CFZ derivatives (Reddy, et al., 1996, Antimicrob. Agents Chemother. 40:633-636; Van Rensburg, et al., 2000, Chemother. 46:43-48: and Zeis, et al., 1987, Antimicrob. Agents Chemother. 31:789-793). In the present study, a more soluble analog of CFZ with a similar redox potential was described. In one embodiment, this analog is effective against tuberculosis in bacterial culture and animal models. Such analogs may also have anti-inflammatory effects on neutrophils, macrophages, and lymphocytes, and act as an immunosuppressant.

Compounds

The compounds of the invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), or a salt or solvate thereof:

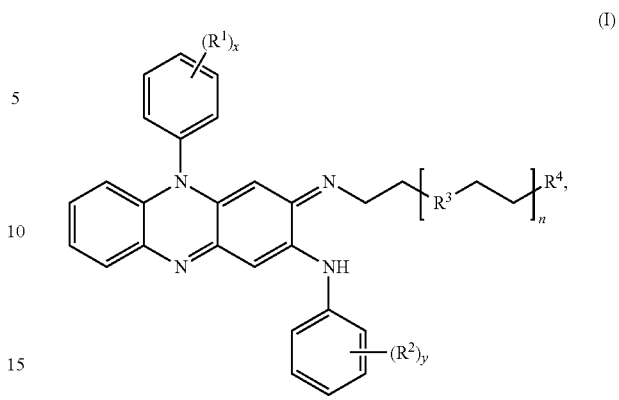

wherein:

each occurrence of $R^1$ and $R^2$ is independently selected from the group consisting of F, Cl, Br, I, CN, $NO_2$, $OR^5$, $SR^5$, $S(=O)R^6$, $S(=O)_2R^6$, $NHS(=O)_2R^6$, $C(=O)R^5$, $OC(=O)R^5$, $CO_2R^5$, $OCO_2R^6$, $N(R^5)_2$, $C(=O)N(R^5)_2$, $OC(=O)N(R^5)_2$, $NHC(=O)NH(R^5)$, $NHC(=O)R^5$, $NHC(=O)OR^5$, $C_1$-$C_6$ alkyl, $C_1$-$C_6$ fluoroalkyl and $C_1$-$C_6$ heteroalkyl;

each occurrence of $R^3$ is independently selected from the group consisting of $N(R^5)$, $CH_2N(R^5)$, O, and $CH_2O$;

$R^4$ is selected from the group consisting of $(CH_2)_mOR^5$, $(CH_2)_mN(R^5)_2$, and $(CH_2)_mNR^5C(C=N^5)N(R^5)_2$;

each occurrence of $R^5$ is independently selected from the group consisting of H, $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of $R^6$ is independently selected from the group consisting of $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl. $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of x and y is independently selected from the group consisting of 0, 1, 2, and 3;

n is an integer ranging from 0 to 4; and m is an integer ranging from 0 to 3.

In one embodiment, each occurrence of $R^1$ and $R^2$ is independently selected from the group consisting of F, Cl, Br, I, CN, $NO_2$, COOH, $C(=O)NH_2$ and $C(=O)NH$—$C_1$-$C_6$ alkyl.

In one embodiment, $R^4$ is selected from the group consisting of OH, $NH_2$, $NHC(C=H)NH_2$ and $(CH_2)_2NHC(C=H)NH_2$.

In one embodiment, the compound of formula (I) is selected from the group consisting of:

(Z)-3-((2-(2-(2-aminoethoxy)ethoxy)ethyl)imino)-N,5-bis(4-chlorophenyl)-3,5-dihydrophenazin-2-amine;

(Z)—$N^1$-(2-aminoethyl)-$N^2$-(2-((10-(4-chlorophenyl)-3-((4-chlorophenyl)amino)phenazin-2(10H)-ylidene)amino)ethyl)ethane-1,2-diamine;

(Z)—$N^1$-(2-aminoethyl)-$N^2$-(2-((10-(phenyl)-3-((phenyl)amino)phenazin-2(10H)-ylidene)amino)ethyl)ethane-1,2-diamine;

(Z)-1-(2-((10-(4-chlorophenyl)-3-((4-chlorophenyl)amino)phenazin-2(10H)-ylidene)amino)ethyl)guanidine;

(Z)-1-(2-((10-(phenyl)-3-((phenyl)amino)phenazin-2(10H)-ylidene)amino)ethyl)guanidine;

(Z)—N¹-(3-((10-phenyl-3-(phenylamino)phenazin-2(10H)-ylidene)amino)propyl)butane-1,4-diamine;
(Z)-1-(4-((3-((10-phenyl-3-(phenylamino)phenazin-2(10H)-ylidene)amino)propyl)amino)butyl)guanidine;
(Z)-1-(2-(2-(2-((10-(4-chlorophenyl)-3-((4-chlorophenyl)amino)phenazin-2(10H)-ylidene)amino)ethoxy)ethoxy)ethyl)guanidine;
(Z)-1-(2-(2-(2-((10-(4-nitrophenyl)-3-((4-nitrophenyl)amino)phenazin-2(10H)-ylidene)amino)ethoxy)ethoxy)ethyl)guanidine;
(Z)-1-(2-(2-(2-((10-(phenyl)-3-((phenyl)amino)phenazin-2(10H)-ylidene)amino)ethoxy)ethoxy)ethyl)guanidine;
(Z)-1-(2-(2-(2-((10-(4-carboxyphenyl)-3-((4-carboxyphenyl)amino)phenazin-2(10H)-ylidene)amino)ethoxy)ethoxy)ethyl)guanidine;
(Z)-1-(2-(2-(2-((10-(4-hydroxyphenyl)-3-((4-hydroxyphenyl)amino)phenazin-2(10H)-ylidene)amino)ethoxy)ethoxy)ethyl)guanidine;
(Z)-1-(2-(2-(2-((10-(4-carbamoylphenyl)-3-((4-carbamoylphenyl)amino) phenazin-2(10H)-ylidene)amino)ethoxy)ethoxy)ethyl)guanidine;
(Z)-1-(2-((10-(4-nitrophenyl)-3-((4-nitrophenyl)amino)phenazin-2(10H)-ylidene)amino)ethyl)guanidine;
(Z)-1-(2-((10-(4-carboxyphenyl)-3-((4-carboxyphenyl)amino)phenazin-2(10H)-ylidene)amino)ethyl)guanidine;
(Z)-1-(2-((10-(4-carbamoylphenyl)-3-((4-carbamoylphenyl)amino)phenazin-2(10H)-ylidene)amino)ethyl)guanidine;
(Z)-1-(2-((10-(4-(N-methyl)carbamoylphenyl)-3-((4-(N-methyl)carbamoylphenyl)amino)phenazin-2(10H)-ylidene)amino)ethyl)guanidine;
(Z)-1-(2-((10-(4-hydroxyphenyl)-3-((4-hydroxyphenyl)amino)phenazin-2(10H)-ylidene)amino)ethyl)guanidine;
combinations thereof, and a salt or solvate thereof.

Preparation of the Compounds of the Invention

The compound of the invention may be prepared according to the methodology outlined in FIG. 20 (the following compounds are referred to as labeled in FIG. 20). Reaction of ortho-bromoaniline (1) with p-bromoaniline (2) and palladium (II) acetate yielded (3) in 63% yield. Reduction of the nitro functionality using zinc dust and hydrochloric acid led to the formation of diamine (4) in quantitative yield. Oxidative dimerization of (4) with ferric chloride and hydrochloric acid yielded (5), which on reaction with isopropylamine (6) under acidic conditions gave the analog (7) (KS1). Separate reaction of (5) with undecylamine (8) and aniline (10) yielded analogs (9) (KS2) and (11) (KS3), respectively. Reaction of (5) with 2,2'-(ethane-1,2-diylbis(oxy))diethanamine (12) under acidic conditions yielded analog (13) (KS4). Oxidative dimerization of the known diamine (14) yielded (15), which on reaction with (12) under acidic conditions gave 16 (KS5). Analog (21) (KS6) was prepared analogously to KS4 and KS5. Reaction of ortho-bromonitrobenzene (1) with p-chloroaniline (17) using palladium acetate yielded (18), which on reduction with zinc yielded (19). Oxidative dimerization of (19) yielded (20), which was reacted with (12) under acidic conditions to yielded (21) (KS6).

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a pro drug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

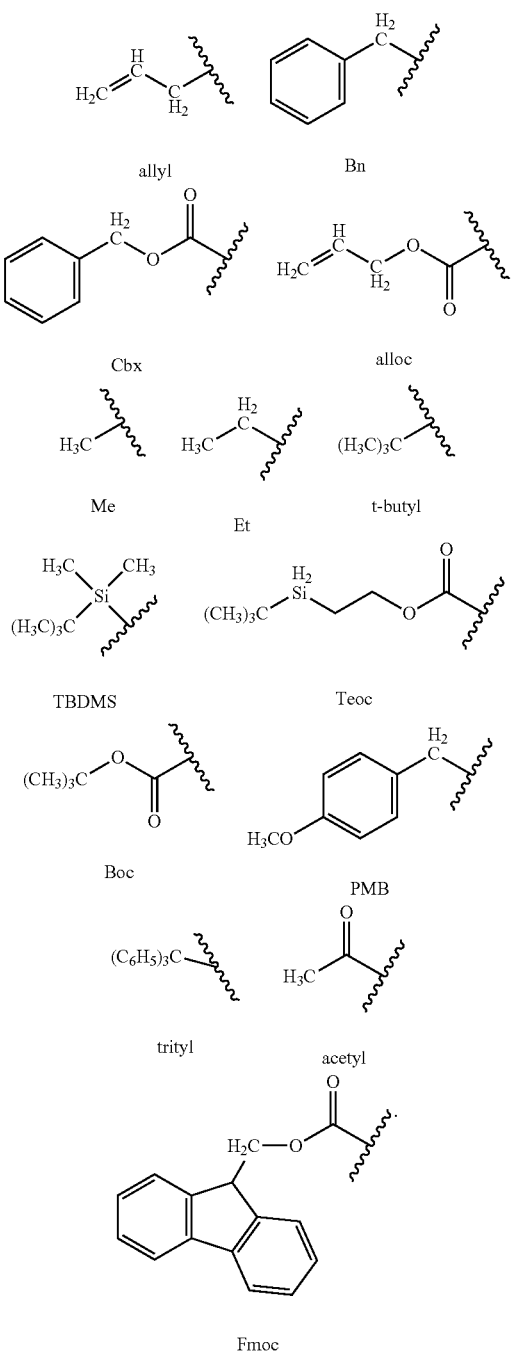

Other protecting groups, plus a detailed description of techniques applicable to the creation of protecting groups and their removal are described in Greene and Wuts, Protective Groups in Organic Synthesis, 3rd Ed., John Wiley &

Sons, New York, N.Y. 1999, and Kocienski, Protective Groups, Thieme Verlag, New York, N.Y., 1994, which are incorporated herein by reference for such disclosure.

Methods of the Invention

The invention includes a method of treating or preventing a *mycobacterium* infection in a subject in need thereof, comprising administering to the subject a therapeutically effective amount of a pharmaceutically acceptable composition comprising a compound of formula (I) or a salt or solvate thereof, whereby the *mycobacterium* infection is treated or prevented in the subject.

The invention also includes a method of treating or preventing a Gram-positive bacterium infection in a subject in need thereof, comprising administering to the subject a therapeutically effective amount of a pharmaceutically acceptable composition comprising a compound of formula (I) or a salt or solvate thereof, whereby the Gram-positive bacterium infection is treated or prevented in the subject.

The invention also includes a method of treating or preventing an yeast infection in a subject in need thereof, comprising administering to the subject a therapeutically effective amount of a pharmaceutically acceptable composition comprising a compound of formula (I) or a salt or solvate thereof, whereby the yeast infection is treated or prevented in the subject.

The invention also includes a method of treating or preventing an inflammatory condition in a subject in need thereof, comprising administering to the subject a therapeutically effective amount of a pharmaceutically acceptable composition comprising a compound of formula (I) or a salt or solvate thereof, whereby the inflammatory condition is treated or prevented in the subject.

The invention also includes a method of treating or preventing an auto-immune disorder in a subject in need thereof, comprising administering to the subject a therapeutically effective amount of a pharmaceutically acceptable composition comprising a compound of formula (I) or a salt or solvate thereof, whereby the auto-immune disorder is treated or prevented in the subject.

The invention also includes a method of treating or preventing a proliferative disease in a subject in need thereof, comprising administering to the subject a therapeutically effective amount of a pharmaceutically acceptable composition comprising a compound of formula (I) or a salt or solvate thereof, whereby the proliferative disease is treated or prevented in the subject.

In one embodiment, the subject is a mammal. In another embodiment, the subject is human.

The compounds of the present invention are further intended to be useful in combination with one or more additional compounds useful for treating a condition considered herein. These additional compounds may comprise compounds of the present invention or compounds known to treat, prevent, or reduce the symptoms or effects of the conditions considered herein.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a condition considered herein. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a condition considered herein in the patient. An effective amount of the therapeutic compound necessary to achieve a therapeutic effect may vary according to factors such as the state of the disease or disorder in the patient; the age, sex, and weight of the patient; and the ability of the therapeutic compound to treat a condition considered herein in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a condition considered herein in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 μg to about 10,000 mg, about 20 μg to about 9.500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1.000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating Parkinson's Disease) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a condition considered herein in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of Parkinson's Disease. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the patient, the current medical condition of the patient and the progression of a condition considered herein in the patient being treated. The skilled artisan will be able to determine appropriate dosages depending on these and other factors.

A suitable dose of a compound of the present invention may be in the range of from about 0.01 mg to about 5.000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 100/%-100%, including, by way of example only, 10%, 15%,20%,25%,30%, 35%,40%, 45%,50%,55%, 60%, 65%,70%,75%,80%, 85%,90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly inhibitors exhibiting high therapeutic indices are preferred. The data obtained from cell culture assays and animal studies is optionally used in formulating a range of dosage for use in human. The dosage of such capsid assembly inhibitors lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

CFZ, HRP, and bovine liver superoxide dismutase were from Sigma-Aldrich. Trifluoperazine (TPZ) was from LKT Laboratories (St. Paul, Minn.), and Amplex Red was from Invitrogen. The bioluminescence ATP detection kit CLS II and proteinase inhibitor mixture (complete EDTA-free) were from Roche Applied Science. Culture media and agar were from Difco. BCA kit for protein measurement was from Pierce. TALON resin was from BD Biosciences. Big CHAP was from Anatrace (Maumee, Ohio).

Solvents used for extraction and purification were HPLC grade from Fisher. Unless otherwise indicated, all reactions were run under an inert atmosphere of Argon. Anhydrous tetrahydrofuran, ethyl ether and toluene were obtained via passage through an activated alumina column. Commercial reagents were used as received. Deuterated solvents were obtained from Cambridge Isotope labs. Merck pre-coated silica gel plates (250 mm, 60 $F_{254}$) were used for analytical TLC. Spots were visualized using 254 nm ultraviolet light, with either anisaldehyde or potassium permanganate stains as visualizing agents. Chromatographic purifications were performed on Sorbent Technologies silica gel (particle size 32-63 microns). KS6 was determined to be greater than 95% pure after chromatography. $^1$H and $^{13}$C NMR spectra were recorded at 500 MHz and 125 MHz, respectively, in $CDCl_3$ on a Bruker AM-500 or DRX-500 spectrometer. Chemical shifts are reported relative to internal chloroform ($\delta$ 7.26 for $^1$H, $\delta$ 77.0 for $^{13}$C). Infrared spectra were recorded on a NaCl plate using a Perkin-Elmer 1600 series Fourier transform spectrometer. High resolution mass spectra were obtained on an Autospec high-resolution double-focusing electrospray ionization/chemical ionization spectrometer with either DEC 11/73 or OPUS software data system. Melting points were obtained on a Thomas Hoover capillary melting point apparatus and are uncorrected.

Growth of Bacteria and Isolation of Membranes:

Typically, M. smegmatis (strain $mc^2$ 155 from ATCC) was grown aerobically in a batch method at 37° C. in 7H9 media supplemented with 0.2% glycerol and 0.1% Tween 80. Growths were monitored at 600 nm; bacteria reaching roughly 0.8 OD were in mid-log phase and those reaching 1.2-1.5 OD were in stationary phase under the conditions and media used in these experiments. Bacteria were harvested by centrifugation at 9,600×g using a JA 10 rotor and Beckman-Coulter J25 centrifuge. Pellets ranging from 12-15 g were then suspended in 100 ml of buffer (10 mM HEPES, pH 7.0, 50 mM KCl, 5.0 m mM $MgCl_2$, and 10% glycerol) containing protease inhibitors and 1.5 mg/ml lysozyme. After incubation at 37° C. for 1 h, the bacteria were lysed in a French Press (three passes) at roughly 1,500 psi. Heavy debris was removed by centrifugation at 9,600×g in a JLA 16.250 rotor (20 min at 4° C.), and lighter materials were removed by centrifugation of the resulting supernatant at 39,000×g in a JA 25.50 rotor (20 min at 4° C.). Membranes in the supernatant obtained above were pelleted by ultracentrifugation at 125,000×g using a 50.2Ti rotor and Beckman L8-80 M preparative ultracentrifuge. The brownish membrane pellet was resuspended in 3-6 ml of buffer, and aliquots of the mixture were snap frozen and stored in liquid nitrogen.

Membrane preparations had the following characteristics after resuspension. The protein concentration of resuspended membranes ranged from 7.5-20 mg/ml as determined by the BCA method. Difference spectra (dithionite reduced minus air oxidized) of membranes showed absorbance peaks characteristic of cytochromes b, c, and a (Weinstein, et al., 2005, Proc. Nat. Acad. Sci. U.S.A. 102:4548-4553). Based on the absorbance of cytochrome $a+a_3$, the concentration of cytochrome $aa_3$ oxidase was between 2-5 µM. Membrane preparations exhibited an active oxidative phosphorylation pathway, catalyzing the oxidation of NADH and the reduction of $O_2$. Under appropriate conditions, they were able to catalyze the phosphorylation of ADP to ATP using either NADH or succinate as an electron donor. ATP synthase activity was measured using the luciferin/luciferase bioluminescence detection system.

Membranes from Escherichia coli, Paracoccus denitrificans, Pseudomonas aeruginosa, and Staphylococcus aureus were prepared in a similar manner to those from M. smegmatis, except that S. aureus was treated with lysostaphin instead of lysozyme to make spheroplasts. All were grown aerobically in LB media at 37° C. to midlog phase. S. cerevisiae was grown in YPD media, and mitochondria and submitochondrial membranes were prepared according to published procedures (Meisinger, et al., 2006, Meth. Mol. Biol. 313:33039; and Pon, et al., 1989, J. Cell Biol. 109: 2603-2616). Rat liver mitochondria were prepared according to published procedures (Johnson, et al., 1967, Methods Enzymol. 10:94-101).

Isolation of Recombinant NDH-2:

Construction of the recombinant expression system of M. tuberculosis type II NADH oxidoreductase (NDH-2) in M. smegmatis and purification of the intact enzyme were described previously (Yano, et al., 2006, J. Biol. Chem. 281:11456-11463). In this study, extraction of NDH-2 from membranes and chromatography on TALON resin were performed using Big CHAP instead of cholate. Big CHAP provided greater enzyme stability than cholate. SDS-PAGE of the purified enzyme demonstrated one major band with an apparent mass of 50 kDa.

Enzyme Assays:

In assays of NADH oxidation, buffer and NADH concentrations were typically 0.1 M HEPES/$Na^+$, pH 7.0, and 250 µM, respectively. The NADH concentration was roughly 10-fold more than the apparent $K_m$ for membrane catalysis of NADH oxidation. Stock membrane preparations (7.5-20 mg/ml) were typically diluted >50-fold in NADH oxidase assays. (Specific protein concentrations in assays are in the figure legends.) A 5.0 mM CFZ stock was made in 100% $Me_2SO$ (DMSO). Additions to assay mixtures were made so that the final $Me_2SO$ concentration was <2%. KCN (2.0 M stock) added to reactions was made fresh in 1.0 M HEPES, pH 7.0. The final KCN concentration of 10-20 mM in reactions inhibited >90% of the membrane catalyzed NADH oxidase activity.

Extinction coefficients ($mM^{-1}$ $cm^-$) used in conversions were 6.22 for NADH consumption at 340 nm; 54 for resorufin formation at 563 nm; 35 for CFZ at 452 nm in 100% EtOH, and 33 for cytochrome $aa_3$ at 604 nm (Mochizuki, et al., 1999, J. Biol. Chem. 274:33409-33411). Absorbance and spectra were recorded using a Beckman DU640 UV-visible spectrophotometer. ROS production was assayed using the Tecan Infinite M1000 plate reader.

Measurement of ROS:

The detection of ROS followed the procedure described by Invitrogen.

The detection system consisted of the dye, Amplex Red, HRP, and superoxide dismutase mixture, which was added to reactions with membranes or purified NDH-2. In this system, HRP catalyzes the stoichiometric reaction of Amplex Red+$H_2O_2$→water+resorufin; the product, resorufin, is monitored at 563 nm. Reactions measuring ROS contained buffer (50 mM HEPES, pH 7.0, and 2.0 mM $MgCl_2$), 50 µM Amplex Red, 80 units/ml superoxide dismutase, and 2 units/ml HRP. Reduced CFZ most likely reacts with $O_2$ to produce the ROS species $O_2^-$ ($O_2+e^-\rightarrow O_2^-$), which is converted to hydrogen peroxide in the presence of superoxide dismutase according to the following reaction: $2O_2^-+2H^+\rightarrow H_2O_2+O_2$ (Amplex Red+$H_2O_2$→water+resorufin). The oxidation of Amplex Red is a two-electron transfer, thus, oxidation of one molecule of NADH ($2e^-$) can produce one molecule of resorufin.

Measurement of M. smegmatis Growth Inhibition by CFZ and INH:

M. smegmatis strain $mc^2$ 155 (ATCC) was grown overnight in Difco Middlebrook 7H9 broth, supplemented with 0.2% glycerol and 0.1% Tween 80. The culture was then

Example 1

Studies on Behavior of CFZ in Water, Detergents, and Membranes

To establish the state of CFZ in reactions with biological membranes, studies were performed to characterize the properties of the drug in buffer, detergents and membranes as a function of pH. CFZ is a weak base existing as a mono-protonated, cationic species and a neutral unprotonated species in the physiological pH range. A pKa value of 8.5 is commonly quoted for CFZ, but this value appears to have an unclear origin. Its c Log P (octanol/water partition ratio) value of 7.53 indicates that the unprotonated species is highly lipophilic. A single study showed that detergent micelles dissolve CFZ (Reddy, et al., 1996, Antimicrob. Agents Chemother. 40:633-636).

CFZ Solubility in Water.

Figure 12A:
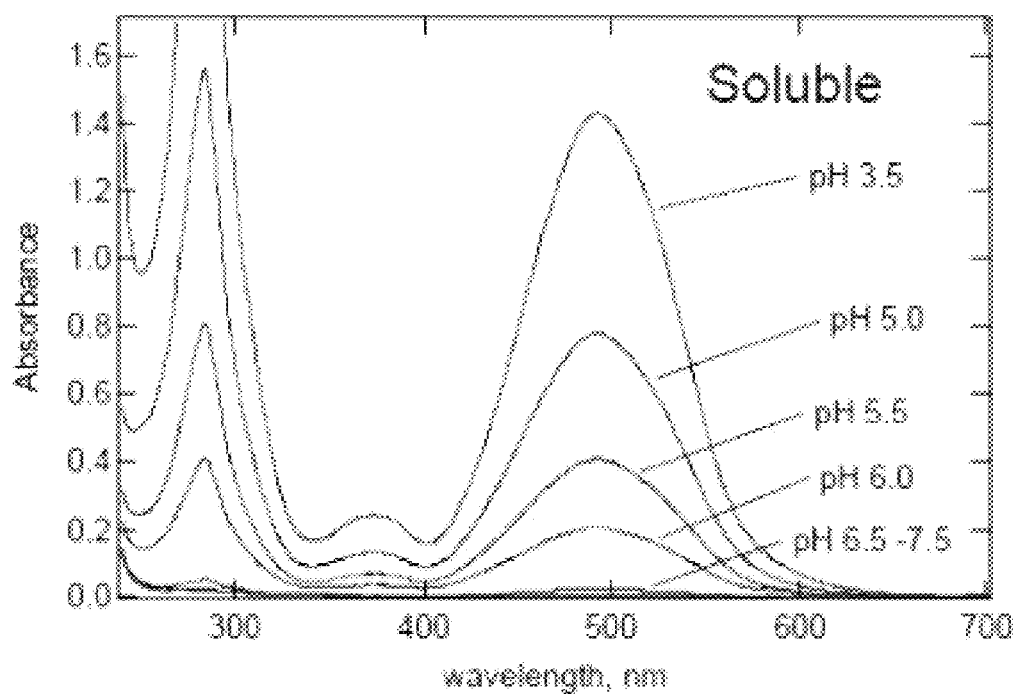
FIGS. 12A-12B, is a series of graphs illustrating the solubility of CFZ dissolved in 0.1 M buffers of various pH values.
Figure 12B:
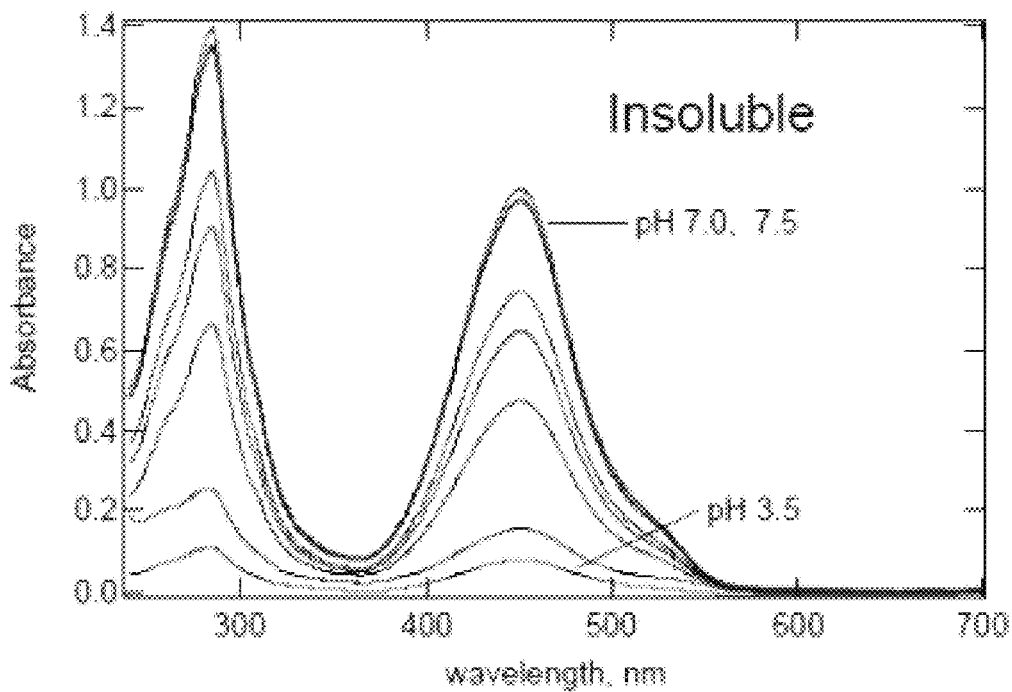

The solubility of CFZ in water as a function of pH is shown in FIG. 12. Stock CFZ was added to solutions of various pH (0.1 M buffer/Na$^+$-MES pH 5.0, 5.5; MOPS pH 6.0-7.0; HEPES pH 7.5; Tricine, pH 8.0, 8.5; and CHES pH 9.0, 9.5 and CAPS, pH 10.0) to produce a concentration equivalent to 50 μM. The solutions were mixed and incubated at room temperature overnight. Soluble and insoluble CFZ were separated by centrifugation, and the procedure was repeated to ensure most, if not all, insoluble material was removed. Pellets were dissolved in 1.0 mL EtOH made alkaline by the addition small amount of CAPS buffer pH 10.0. The absorption spectra of the supernatants and solubilized pellets are shown in FIGS. 12A and 12B respectively. CFZ was most soluble at pH 3.5 where virtually all the drug remained in the supernatant. As the pH increased, CFZ absorbance decreased in the supernatants and increased to a maximum in the pellets. Soluble CFZ was barely detectable at pH 6.5 and not detectable above pH 7.5. The spectrum of water soluble CFZ exhibited two major peaks at 284 and 492 nm, and a minor peak at 373 nm, in agreement with that reported for mono-protonated (cationic) CFZ. The blue shift in the visible spectrum in EtOH-pH 10 for pelleted CFZ is consistent with that of unprotonated CFZ. A similar shift was also observed for CFZ dissolved in octanol and cyclohexane. Thus, at neutral pH, little (<2 μM or below 0.05 A$_{492}$ nm limit) CFZ is soluble in water.

Figure 13A:
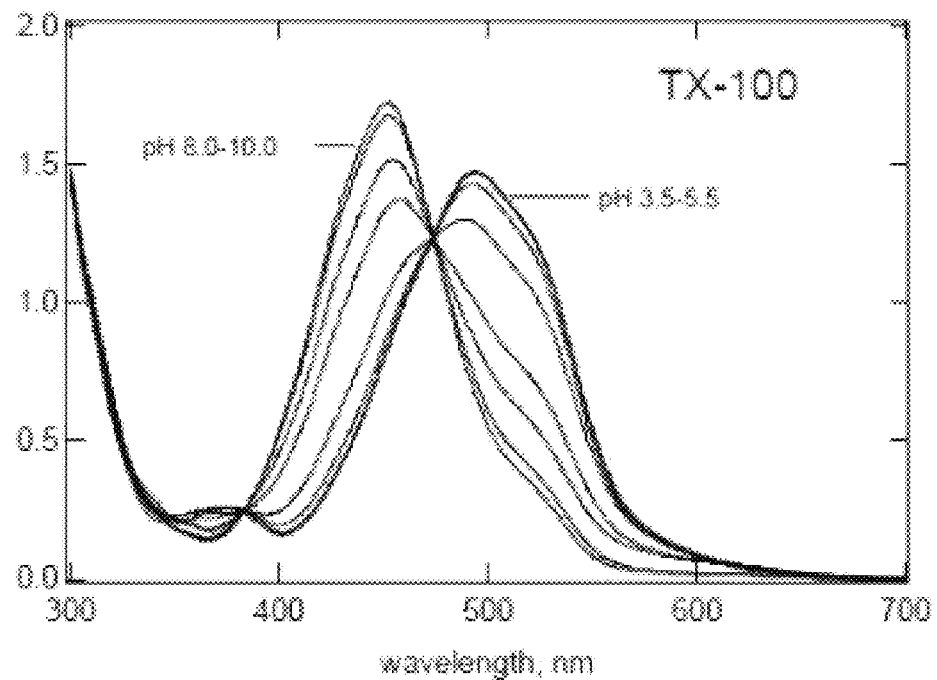
Figure 13B:
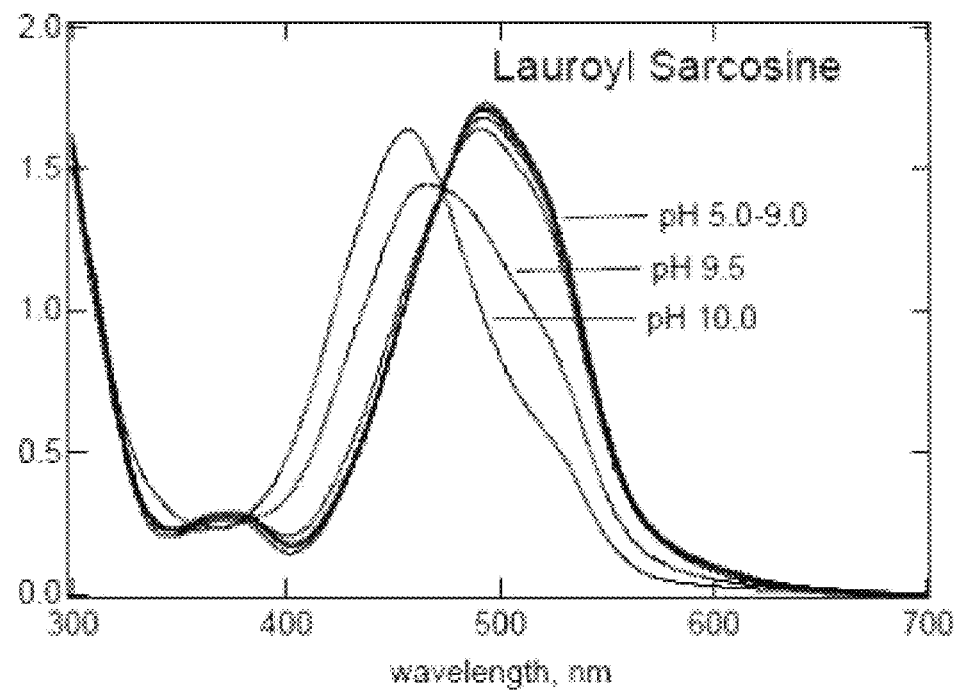

CFZ Solubility in Detergents:

Addition of detergents to buffers increased the solubility of CFZ. At least 50 μM CFZ is soluble over the pH range of 3.5-10.0 in 0.5-1.0% Triton X-100, a neutral detergent, or Na-lauryl sarcosine, a negatively charged detergent. Spectra of CFZ in both detergents are shown in FIGS. 13A and 13B, respectively. In Triton-X 100, two spectra consistent with cationic and unprotonated CFZ species were discernible at low and high pH. Below pH 6.0 spectra exhibited a minor peak at 373 nm and major at 492 nm consistent with that of cationic CFZ, and above pH 8.0 spectra exhibited a major peak at 452 nm, consistent with uncharged CFZ. A progressive shift in the spectra from cationic to uncharged species was observed between pH 6.0 and 8.5. Isosbestic points at 370 and 470 nm indicate a pH transition between two species.

Based on the endpoint spectra, the transition between cationic and uncharged species as a function of pH was quantified (FIG. 13C). The proportion of each species was estimated separately using absorbance values at 435 nm to estimate the proportion of uncharged CFZ and wavelength 500 nm to estimate the proportion of cationic CFZ according to equation 1. The results plotted in FIG. 13C indicate that titration of a group with an apparent pKa of 6.8 (solid lines fitted through data) governs the proportion of each CFZ species in Triton-X 100. In Na-lauroyl sarcosine, a marked difference in the pH dependence of CFZ was observed. According to the spectra, the cationic form was preferred until pH 10.0, indicating a marked stabilization of this species by roughly 3.0 pH units in the negatively charged detergent.

$$\text{fraction species} = \frac{A_{pH} - A_{min}}{A_{max} - A_{min}} \qquad \text{Equation 1}$$

where absorbances for min and max were determined from endpoint spectra at wavelengths 433 nm for unprotonated CFZ and 500 nm for protonated CFZ and pH is the absorbance at corresponding wavelengths for transition spectra.

Figure 14A:
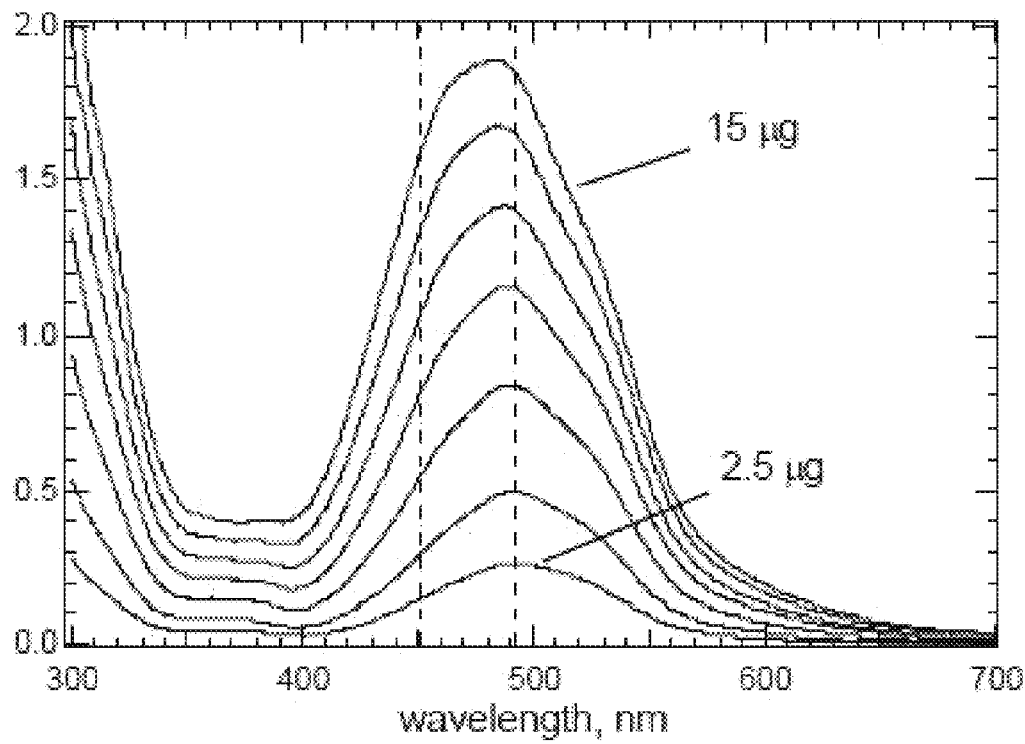
FIGS. 14A-14B, is a series of graphs illustrating binding of CFZ to isolated M. smegmatis membranes.
Figure 14B:
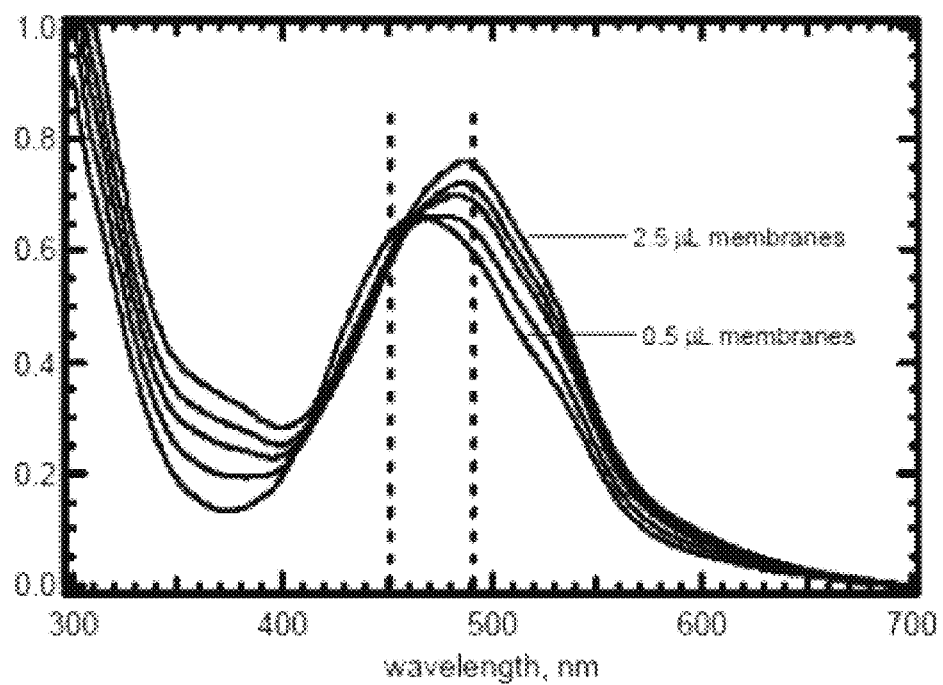
Figure 16:
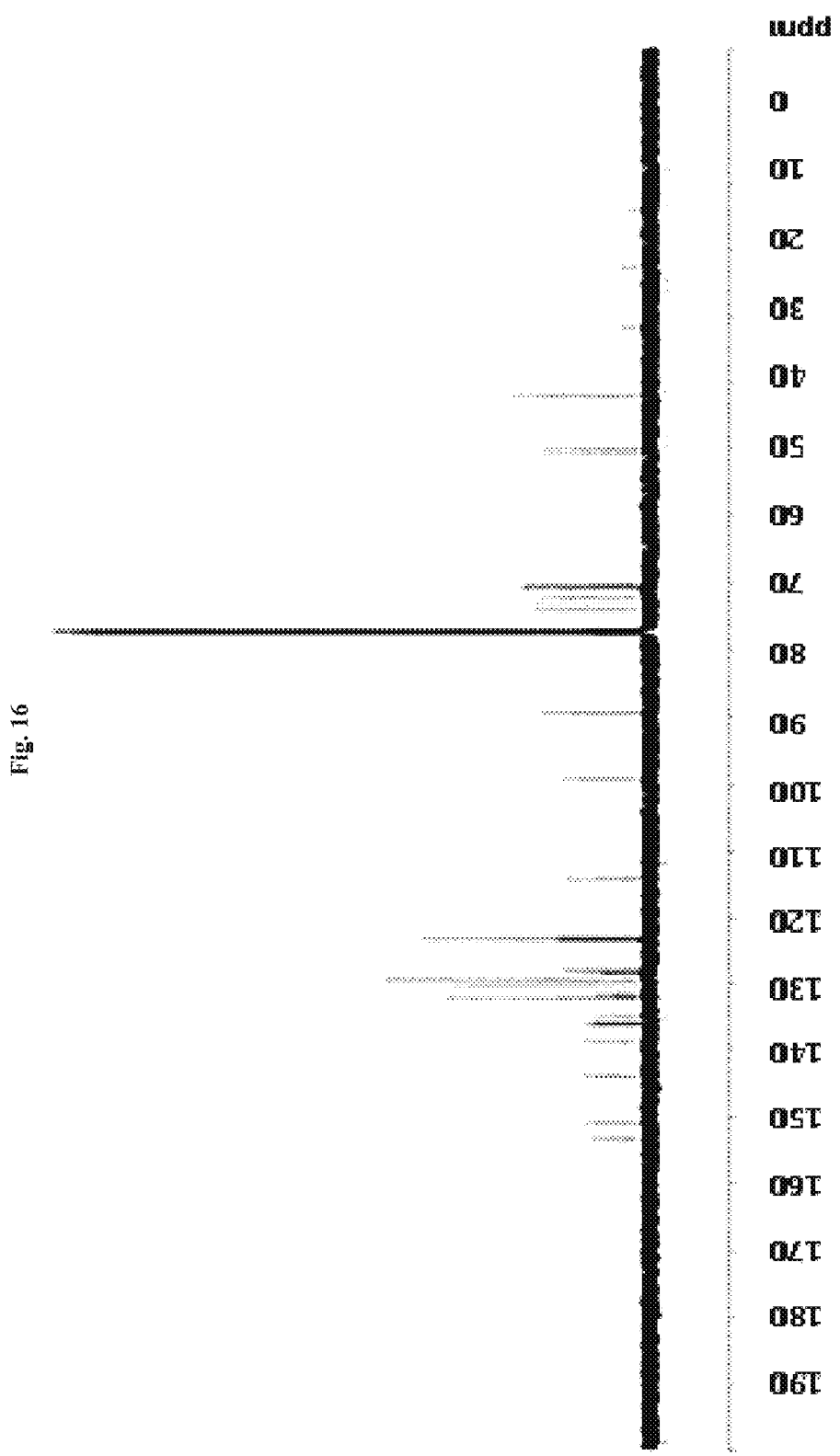
FIG. 16 illustrates the $^{13}C$ NMR (125 MHz, $CDCl_3$) spectrum of KS6.

Binding of CFZ by Membranes:

The interaction of CFZ with *M. smegmatis* membranes at pH 7.0 was characterized in FIG. 14. In FIG. 14A, CFZ was incrementally added to a fixed amount of membrane whereas in FIG. 14B membrane was incrementally added to a fixed amount of CFZ. At the endpoints the incubations were centrifuged to remove any insoluble CFZ. The spectra in FIG. 14A indicate that at low saturation, cationic CFZ is stabilized by membranes. The two vertical lines represent the peak maxima for the uncharged (452 nm) and cationic (492 nm) CFZ species. Upon further addition of CFZ, the spectra show a modest blue shift consistent with some accumulation of uncharged CFZ. Based on the absorbance after centrifugation, an equivalent of about 50 μM CFZ remained in solution associated with the membrane. Deconvolution of the spectra using endpoint spectra in FIG. 14A indicated that approximately 80% of the CFZ was cationic at the end of the experiment. An opposite shift (blue to red) in the spectra was observed in FIG. 14B where CFZ was held constant and membrane was added to the incubation. These results indicated that CFZ is mobile when associated the membrane and that the cationic species is the preferred form bound by membranes at neutral pH and especially at low saturation. Given the behavior of CFZ in neutral and anionic detergents, the most likely membrane components stabilizing cationic CFZ are negatively charged lipids.

From the study depicted in FIG. 14A and other similar studies not shown, *M. smegmatis* membranes may bind as high as 0.5±0.25 μg CFZ per μg membrane protein. Assuming an equal weight ratio between lipid and protein in the bacterial cytoplasmic membrane, and an average mass of 600 Da for a lipid, the amount of CFZ associated with the membrane at may attain 0.5-1.0 mole of CFZ per mole of lipid. These results suggest that *M. smegmatis* membranes bind substantial amounts of CFZ and that the major species bound at physiological pH is the cationic form, which is the redox active form. Thus CFZ may have the potential to disrupt membranes due to high levels of binding and to interact with respiratory) enzymes due to stabilization of the redox active cationic form.

Example 2

Preparation of 3-(4-Chloroanilino)-10-(4-chlorophenyl)-2-[4-(8-amino-3,6-dioxaoctyl)]imino]-2,10-dihydrophenazine (KS6, 2)

The hydrochloride of 1 (O'Sullivan, J. F., 1984, Chem. Res., Miniprint 52) was converted into amine 2 using the method of O'Sullivan and coworkers (O'Sullivan et al., 1988, J. Med. Chem. 31:567-572; Kamal et al., 2005, Bioorg. Med. Chem. Lett. 15:1923-1926). (95 mg, 47%). $^1$H NMR (CDCl$_1$): δ=7.46 (d, J=8.3 Hz, 4H), 7.26 (m, 6H), 7.13 (m, 2H), 6.80 (s, 1H), 6.43 (dd. J=8.3, 1.1 Hz, 1H), 5.24 (s, 1H), 3.79 (t, J=6.5 Hz, 2H), 3.63 (m, 4H), 3.48 (t, J=5.2 Hz, 2H), 3.31 (t, J=6.5 Hz, 2H), 2.83 (t, J=5.2 Hz, 2H). $^{13}$C NMR NMR (CDCl$_3$): δ=153.4, 151.0, 143.7, 138.7, 136.1, 136.0, 135.8, 134.9, 132.0, 131.4, 130.3, 129.5, 128.6, 128.4, 127.8, 123.3, 123.1, 114.2, 99.3, 89.3, 73.6, 72.3, 70.7, 70.4, 50.3, 41.9. FTIR (thin film) 3414, 1631, 1524, 1246, 756. HRMS (ES) Calcd. for $C_{30}H_{29}Cl_2N_5O_2$: 561.1698 (M$^+$). found 562.1798 (MH$^+$).

Figure 17A:
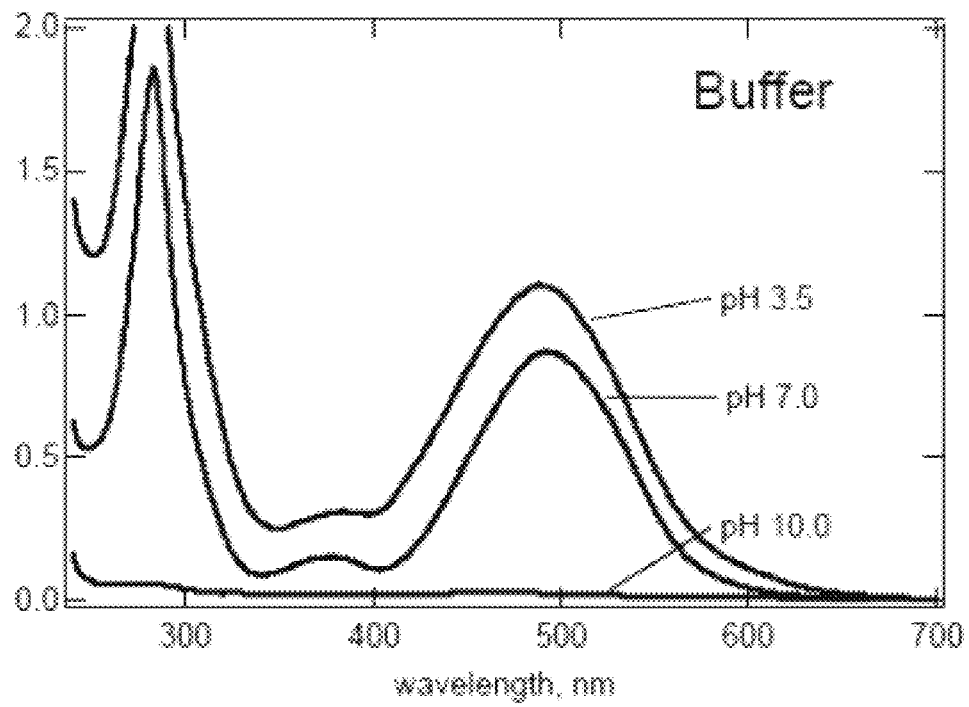
FIGS. 17A-17B, is a series of graphs illustrating the spectra of soluble KS6 at different pH in buffered water and in buffered solutions containing 1% TX-100.

KS6 was analyzed in a similar fashion to CFZ in FIGS. 12 and 13. In FIG. 17A, the solubility of KS6 was measured in solutions of pH 3.5, 7.0, and 10.0. In contrast to CFZ, about 70% of KS6 remained in solution after centrifugation at pH 7.0. Increasing the pH to 10.0 produced complete insolubility, consistent with conversion to fully unprotonated form. The visible spectrum of soluble KS6 at pH 7.0 mirrored that of protonated CFZ. KS6 remained fully soluble when 1% Triton X-100 was added to the solutions. The titration in the TX-100 indicated two spectral species similar to CFZ and a pH dependent transition between both species similar to CFZ. These results indicate that the new group attached to R-imino group did not significantly affect the basic character of the core ring structure. The solubility of KS6 at pH 10 in Triton X-100 also indicated that KS6 interacts with membranes.

Redox cycling KS6 similar to CFZ is shown in FIG. 18. KS6 incubated with *M. smegmatis* membranes was bleached upon addition of NADH. The bleaching was temporary and absorbance returned due to the consumption of NADH permitting the rate of re-oxidation to dominate. A second addition of NADH more completely bleached KS6 because the dissolved O$_2$ was diminished slowing the rate of KS6 re-oxidation relative to the rate reduction. Upon consumption of NADH there was some re-oxidation, but too little O$_2$ present to completely re-oxidize KS6. Agitation to replenish O$_2$ in the reaction resulted in the rapid return of KS6 absorbance. These studies showed that KS6 is a more soluble form of CFZ; like CFZ it is reduced by membrane-bound oxidoreductases, presumably, NDH-2, to a form which is spontaneously re-oxidized by O$_2$.

Example 3

Distribution and Charge of CFZ in Reactions with Isolated Bacterial Membranes

The reactivity of CFZ was difficult to study because of its insolubility in water. The dye is a weak base of neutral charge, with the extremely high calculated octanol/water partition ratio (c Log P) of 7.5, indicating that it is highly lipophilic and dissolves much better in hydrophobic than aqueous environments. Protonation of the base produces a cationic species, which could alter solubility properties. Charged and uncharged species differ in redox potential ($E_m$=−950 mV versus −180 mV for uncharged and cationic species, respectively) with only the cationic species predicted to be redox active under physiological conditions (Kovacic, et al., 1989, Bioelectrochem and Bioenerg. 21:269-278). Therefore, to better understand the state of CFZ in reactions containing isolated bacterial membranes and in live bacteria, the solubility and species composition of CFZ in water, detergents, and membranes were characterized as a function of pH (see Example 1).

Figure 17B:
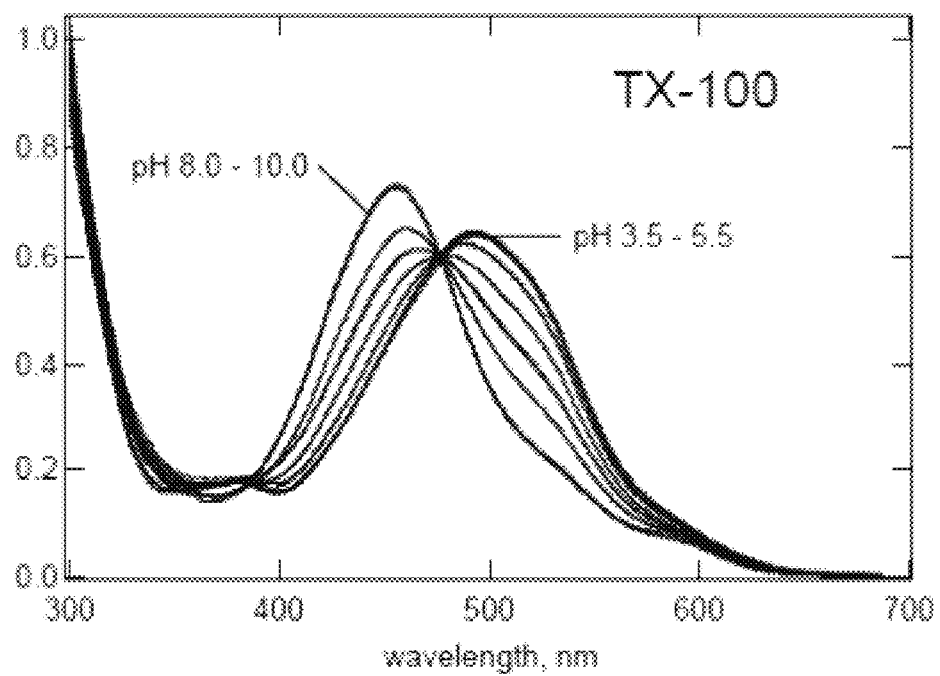
Figure 20A:
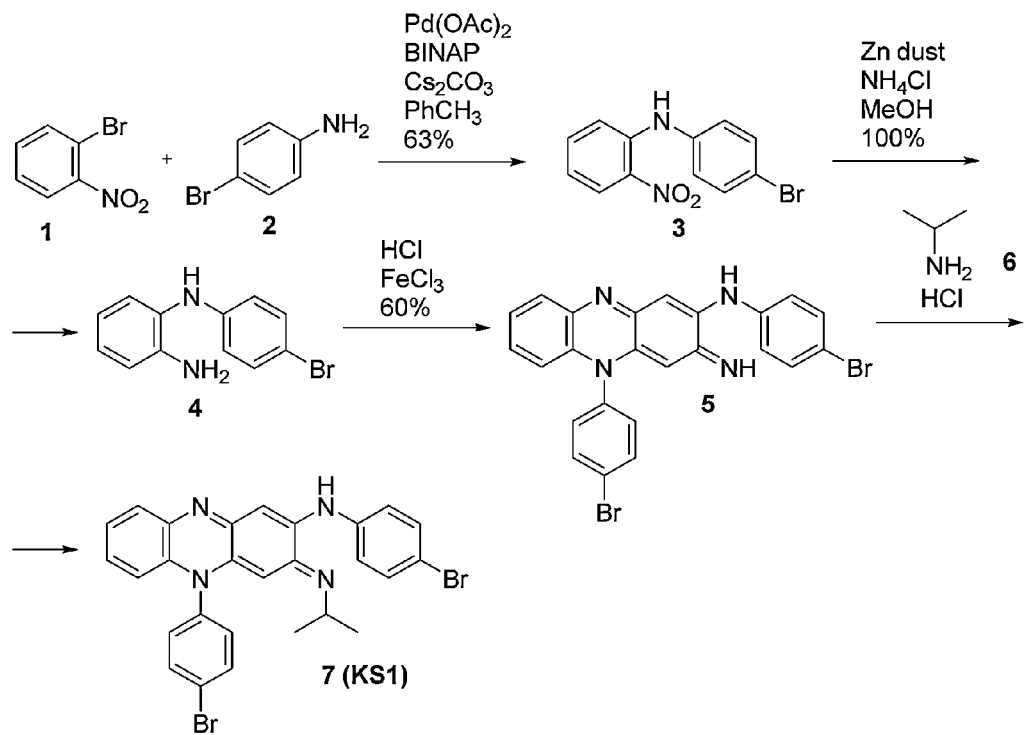
FIGS. 20A-20E, illustrates the synthesis of non-limiting examples of compounds of the invention.
Figure 20B:
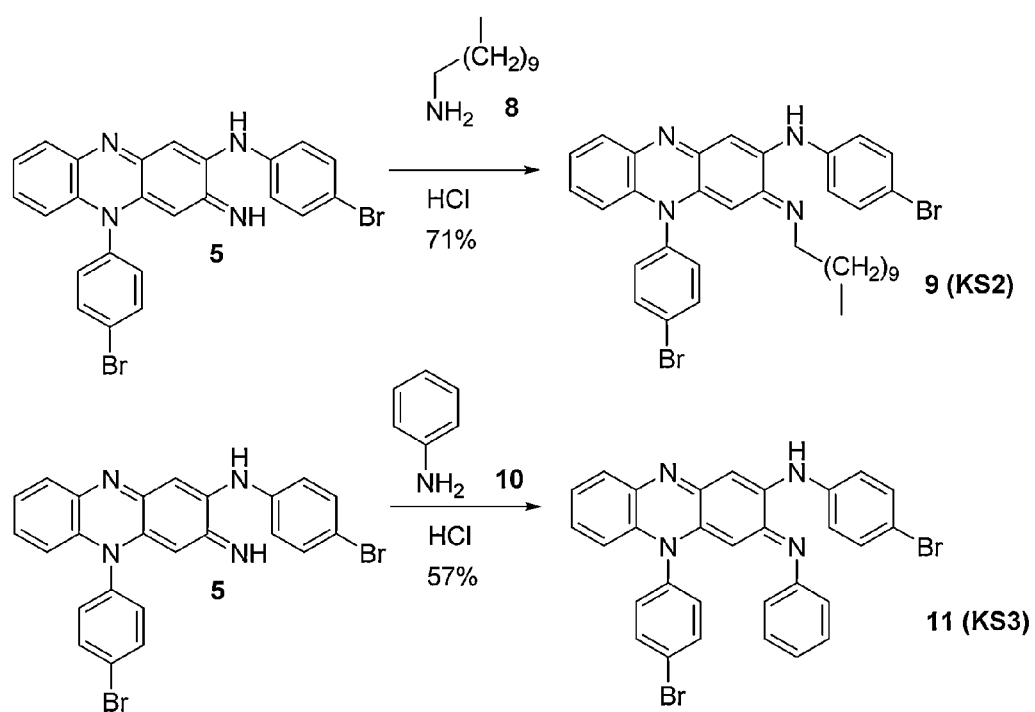
Figure 20C:
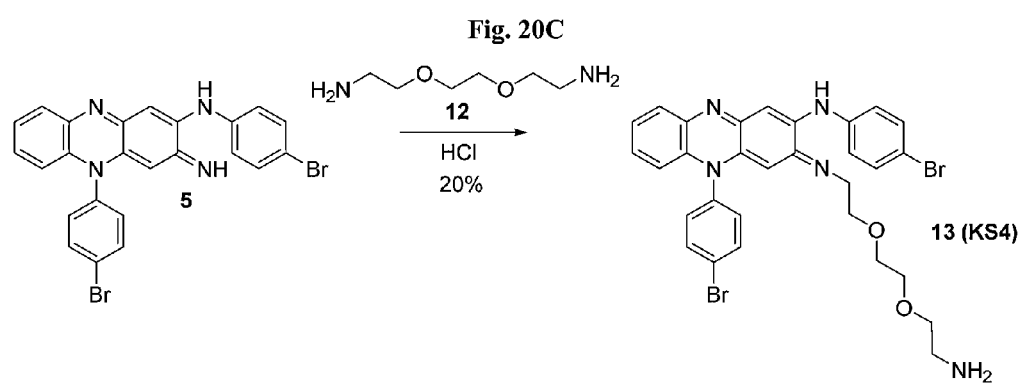
Figure 20D:
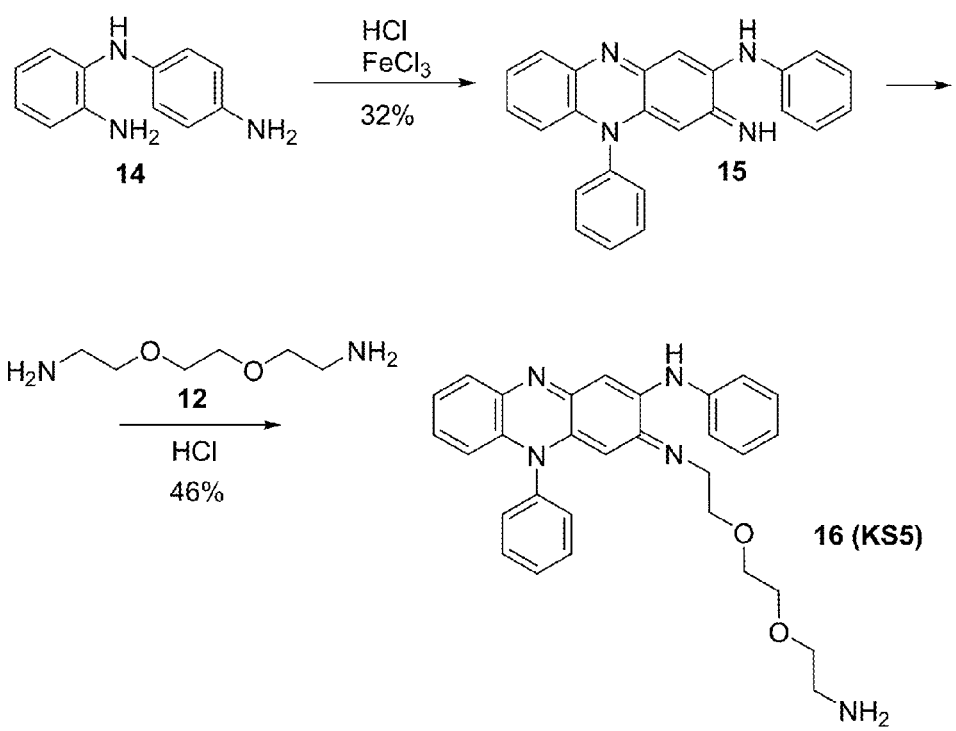
Figure 20E:
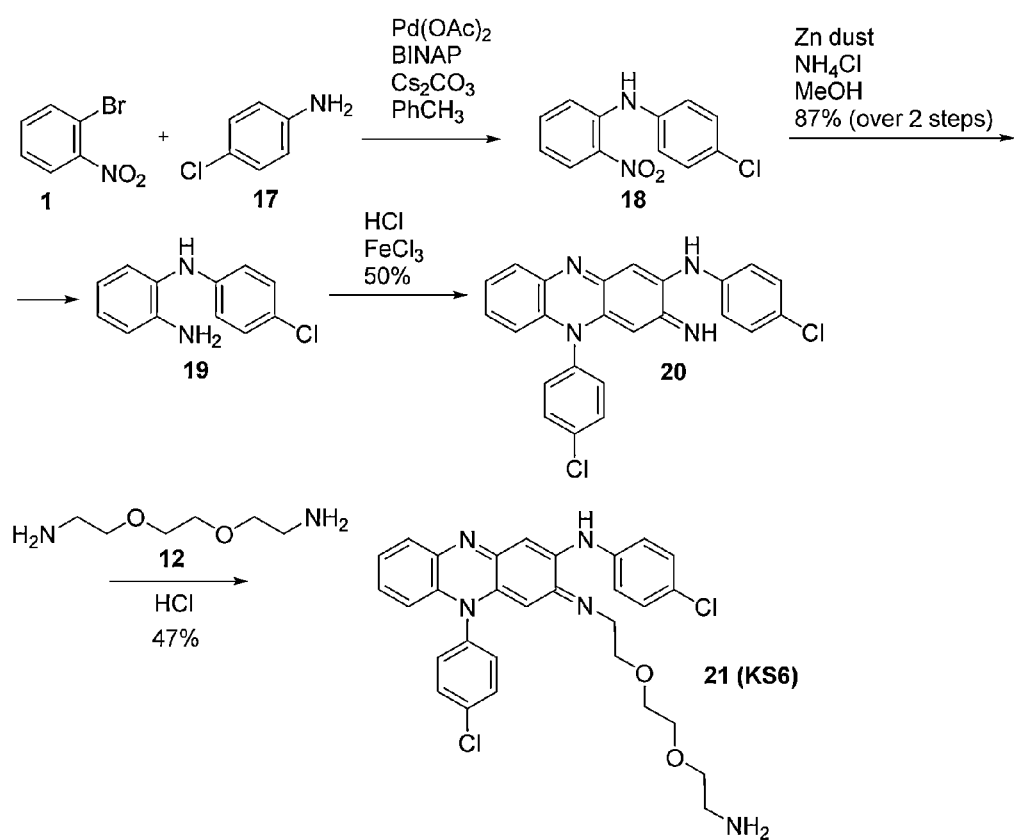

Solubility of CFZ was determined using centrifugation to separate aggregated/precipitated from soluble material and spectroscopy to quantify CFZ. CFZ added to buffer was initially solubilized in DMSO and diluted 100-fold into water containing buffer, detergents, or membranes. Consistent with dissociation of a proton to produce a neutral form, CFZ solubility in water decreased as the pH was raised from 3.5 to 8.0. At pH 7.0, soluble CFZ was near the limit of detection (absorbance of 0.025 at 492 nm). Below pH 7.0, the visible spectrum of buffer-soluble CFZ reflected that reported for the cationic species (Rhodes, et al., 1973, Biochem. Pharmacol. 22:1047-1056; and Morrison, et al., 1976, Int. J. Lepr., 44:475-481). In agreement with a previous study (Fahelelbom, et al., 1993, Pharma. Res., 10:631-634), CFZ solubility increased markedly in the presence of a neutral (Triton X-100) and an anionic detergent (lauroyl sarcosine). A concentration of at least 50 μM CFZ was soluble in 0.5-1.0% (w/v) detergents over the pH range of 5.0-10.0. Two spectral species consistent with cationic and neutral forms of CFZ were observed in Triton-X 100, and their proportion appeared modulated by the titration of a group with pK$_a$ of 6.8. In contrast to Triton X-100, cationic CFZ dominated in anionic detergents until pH 10.0, indicating its stabilization by roughly 3.0 pH units relative to Triton X-100. Addition of isolated membranes from *M. smegmatis* or *E. coli* to solutions also increased the solubility of CFZ. Similar to anionic detergents, membranes at pH 7.0 preferred to bind cationic CFZ especially at low FZ/membrane ratios (FIG. 17), suggesting stabilization by negatively charged lipids. Solubilization and stabilization of cationic species sheds light on how the redox active form can exist at pH 7.0. The amount of CFZ incorporated into *M. smegmatis* membranes was substantial and estimated from the studies to be as high as 0.5 μg/μg membrane protein at pH 7.0. Because CFZ is mostly membrane bound in the reactions reported herein, the reporting of a CFZ concentration in reactions would be misleading. Therefore, in the studies CFZ is reported as μg added to a reaction volume. In reactions, CFZ did not exceed its predicted membrane saturation level unless noted.

Example 4

Effect of CFZ on NADH Oxidation Catalyzed by Isolated Bacterial Membranes

Early work with CFZ reported partial restoration of O$_2$ consumption when the compound was added to cultures of *M. tuberculosis* treated with KCN; a result suggesting the reduction of CFZ by the respiratory chain (Barry, et al., 1957. Nature, 179:1013-1015). To further investigate this possibility, the effect of CFZ on the respiratory chain activity of membranes isolated from *M. smegmatis* and *E. coli* were examined.

Membranes from both *M. smegmatis* and *E. coli* catalyzed the oxidation of NADH measured by loss of absorbance at 340 nm (FIG. 2). NADH oxidation was ≥90/% inhibited by KCN addition, indicating that most of the activity was mediated by respiratory chain enzymes transferring electrons to $O_2$. Addition of CFZ to inhibited *M. smegmatis* membranes restored a significant level of NADH oxidation, as shown by increases in the rate of absorbance decrease relative to that remaining after KCN addition (FIG. 2A). NADH (250 μM) in the reaction was in molar excess of CFZ, which was equivalent to 40 μM after all additions. Despite the difference, NADH was continuously consumed until it was fully oxidized when reactions were monitored for longer times. Thus, CFZ acted in a catalytic manner to provide a new path for electrons from NADH to exit the respiratory chain. By comparison, cyanide-inhibited *E. coli* membranes showed no restoration of NADH oxidation upon CFZ addition, consistent with the bacterial specificity of CFZ (FIG. 2B).

The CFZ-related increases in NADH oxidase activity in FIG. 2A and similar experiments with different membrane preparations were quantified, and the data were presented in FIG. 3A as the fraction of NADH activity restored by addition of CFZ. NADH oxidation rates were estimated from the slopes of lines generated in studies similar to those in FIG. 2A. The points at 0.0 CFZ is the NADH oxidase activity remaining after addition of KCN. Membranes in reactions had roughly the same starting NADH oxidase activity; that is, the amount of membrane added in reactions produced a decrease in 340 nm absorbance of ~0.1/min. A relatively large range of CFZ additions was used to study effects on NADH oxidase activity as membrane levels approached (and possibly slightly exceeded) saturation. By estimate, saturation was approached at ~5.0 μg of CFZ.

*M. smegmatis* membranes derived from log and stationary phase growth was studied to determine whether stage of growth affected membrane reactivity with CFZ. Sets 1 and 2 in FIG. 3A refer to chronologically separated studies involving several membrane preparations derived from time-monitored growths. Set 1 consists of three preparations: two from cultures grown into stationary phase and one from a culture grown into mid-log phase. The data presented for the stationary phase membranes is the average±S.E. of five measurements (three with one preparation and two with the other). The data illustrated in FIG. 2A is included in the above measurements. The log growth data was the average±S.D. of three measurements made with the one mid-log phase growth. Set 2 consisted of six separate membrane preparations; three were grown into stationary phase, and three were grown into mid-log phase. Both the stationary and log data presented were the average±S.D. of three measurements, one with each membrane preparation.

All membrane preparations showed significant restoration of NADH oxidase activity. Although the extent of activity restoration differed between log and stationary phase membranes, profiles were similar exhibiting a progressive increase to a maximum followed by a plateau or slight decline. The progressive increase may be due to the rapid accumulation of the cationic CFZ species (redox active) in membranes at low saturation levels, whereas the flattening/decline may be the result of a limit on membrane incorporation of the cationic form coupled with possible adverse effects on membrane integrity (fluidity and or porosity) affecting enzyme reactions. It is important to note that even at high amounts of added CFZ, NADH oxidase activity continued.

A more soluble form of CFZ (referred to as KS6) was synthesized by replacing the R-imino isopropyl group with an aminoethoxylethoxyethyl group. The modification was not expected to change the redox characteristics, and as illustrated in FIG. 3B, KS6 restored NADH oxidation in reactions with KCN-treated membranes. NADH oxidase activity generated by KS6 increased more gradually than CFZ, and the dose-dependent profile appeared more characteristic of an enzyme-substrate interaction, perhaps reflecting its greater water solubility.

The ability of log phase membranes from both studies (sets 1 and 2) to restore NADH oxidase activity was similar (maximum of 0.25). Restoration levels derived from stationary phases were higher (maximum of 0.40-0.70) but varied. The reason for membrane variation in extent of restoration may be unclear. In a non-limiting aspect, the transition from log to stationary phase does not completely explain the variation, though it may contribute. It cannot be discounted that the high pressure method needed to disrupt mycobacteria may lead to variable extents of membrane damage and compositional differences among preparations. Variation in NADH oxidase activity restoration levels was also noted in preparations where growth phase was not carefully documented. In these preparations, restoration was never less than that observed for log phase membranes and sometimes approached that of the most active stationary phase. Regardless of the reason for the variation, the rate of CFZ-mediated NADH oxidase activity in all membrane preparations was on scale with the rate of the electron transport chain at saturating levels of NADH. Thus, CFZ-mediated NADH oxidase activity could have consequential effects on mycobacterial physiology.

Figure 4:
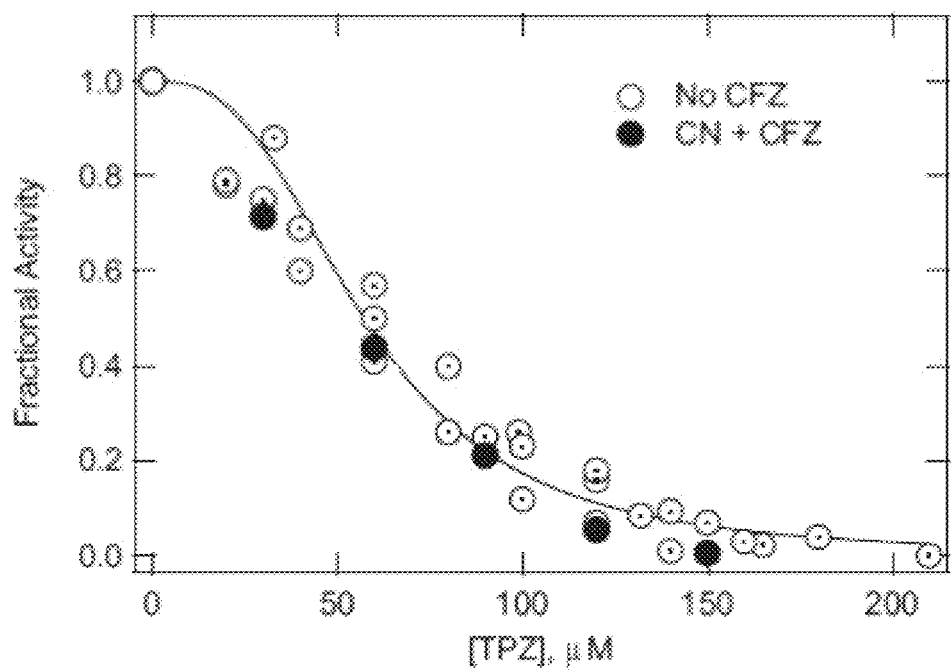
FIG. 4 is a graph illustrating TPZ inhibition of *M. smegmatis* NADH oxidase activity in the absence and presence of KCN/CFZ. Reactions, 250 µl total volume, contained 0.1 M HEPES pH 7.0, 225 µM NADH, and *M. smegmatis* membranes (10 µg membrane protein) from a preparation highly reactive with CFZ (see FIG. 2). NADH oxidase rates (loss/min of absorbance at 340 nm) were measured from time-courses as shown in FIG. 1. TPZ was added to reactions without (open circles) or with KCN/CFZ (20 mM/0.5 µg, filled circles). Fractional activity is the rate of absorbance loss in presence of TPZ relative to the control without TPZ. Line fit through the data were obtained using the Hill equation with an exponent of 3.0.

Based on previous studies, it was tacitly assumed that the CFZ-mediated NADH oxidase activity involved a respiratory chain oxidoreductase. However, so far, the data do not rule out a nonrespiratory chain enzyme because control NADH oxidase activity measurements were based on the ability to transfer electrons/$H^+$ to $O_2$ and would not measure the activity of an NADH-dependent oxidoreductase requiring a different electron acceptor to function. To directly implicate a respiratory chain enzyme(s), the effect of the drug TPZ on NADH oxidase activity and CFZ-mediated NADH oxidase activity was investigated (FIG. 4). TPZ specifically inhibits the mycobacterial respiratory chain enzyme, NDH-2 (Weinstein, et al., 2005, Proc. Nat. Acad. Sci. U.S.A. 102:4548-4553; and Yano, et al., 2006, J. Biol. Chem. 281:11456-11463). NDH-2 is the primary NADH: quinone oxidoreduction expressed by *M. smegmatis* as well as other mycobacteria (Weinstein, et al., 2005, Proc. Nat. Acad. Sci. U.S.A. 102:4548-4553; and Yano, et al., 2006, J. Biol. Chem. 281:11456-11463) and therefore is responsible for the transfer of electrons from NADH into the electron transport chain. As illustrated in FIG. 4, TPZ inhibited CFZ-mediated NADH oxidase activity in log and stationary membranes similarly to control NADH activity, strongly indicating that a respiratory chain enzyme(s) was interacting with CFZ.

Example 5

Reduction and Oxidation of CFZ by Isolated *M. smegmatis* Membranes

Figure 5:
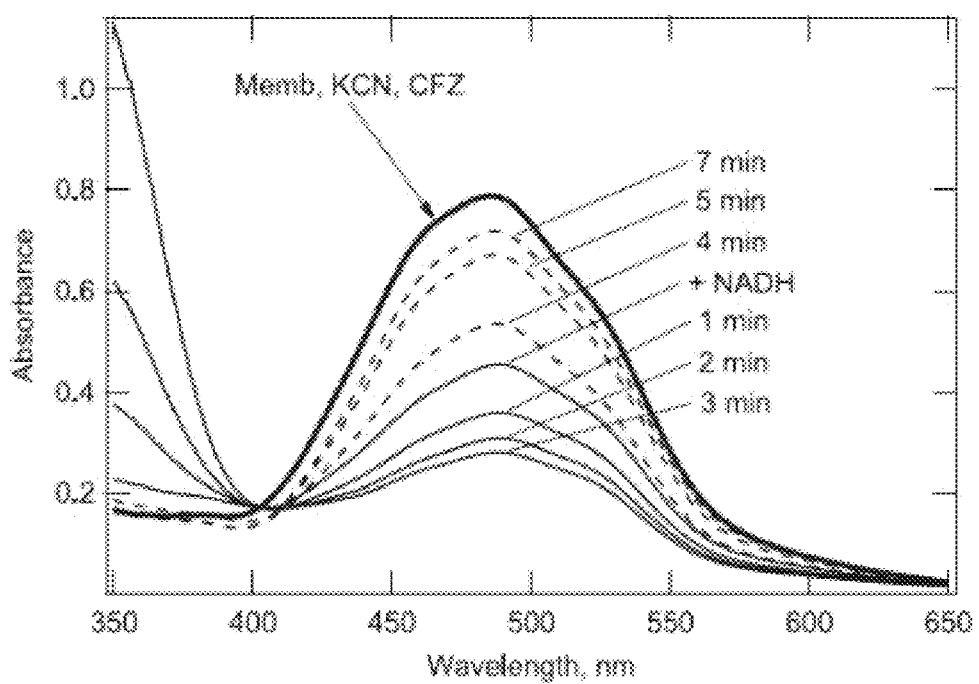
FIG. 5 is a graph illustrating reduction and re-oxidation of CFZ during a reaction with KCN-treated *M. smegmatis* membranes. Spectra were obtained from a single reaction in a total volume of 500 µl monitored over time; background absorbance due to membranes was subtracted. Membranes (Memb, 80 µg membrane protein) from a highly CFZ-responsive preparation were preincubated with 10 mM KCN and 4.8 µg of CFZ; the spectrum did not change with time (thick line). NADH (225 µM) was then added, and the spectrum was recorded immediately (+NADH). Additional spectra were then recorded at ~1.0-min intervals. Absorbance in the region of 350-400 nm is from NADH and that from 400-550 nm is from CFZ. Spectra depicted with a solid line show change in CFZ (reduction phase) correlating with decrease in NADH absorbance, and those depicted with a dotted line show CFZ absorbance change (reoxidation phase) after virtually complete oxidation of NADH.

Given the reported redox properties of CFZ (Barry, et al., 1957, Nature 179:1013-1015: O'Connor, et al., 1995, Drug Metab. Rev. 27:591-614: and Kovacic, et al., 1989, Bioelectrochem and Bioenerg. 21:269-278), NADH oxidation mediated by CFZ likely involves the reduction of CFZ itself and then its spontaneous reoxidation by $O_2$. Evidence for this mechanism of action is presented in FIGS. 5 and 6. The reduction of CFZ during NADH oxidation was demonstrated by the bleaching of the drug during reactions with KCN-treated membranes (FIG. 5). In this study, a relatively large amount of *M. smegmatis* membranes from a preparation that showed high CFZ restoration of NADH oxidase activity was first incubated with KCN and CFZ. The absorption spectrum illustrated in FIG. 5 for these treated membranes reflected that of the redox active cationic form of CFZ (FIG. 5, thick line); the spectrum did not change with time. NADH was then added to the incubation, and spectra were recorded at the times shown. The NADH absorption peak at 340 nm does not overlap with that of CFZ (400-600 nm) in the visible region but is the major contributor to the spectra from 350 to 400 nm. A marked loss of CFZ absorbance was observed after addition of NADH that continued for ~3 min until the NADH became depleted (FIG. 5, solid lines). After this time, the absorbance in the CFZ region of the spectrum began to increase returning to near that of the starting spectrum after 4-7 min (FIG. 5, dashed lines). The bleaching of the visible absorbance spectrum is consistent with the reduction of CFZ, and the return of absorbance is consistent with spontaneous reoxidation of reduced CFZ.

Figure 6A:
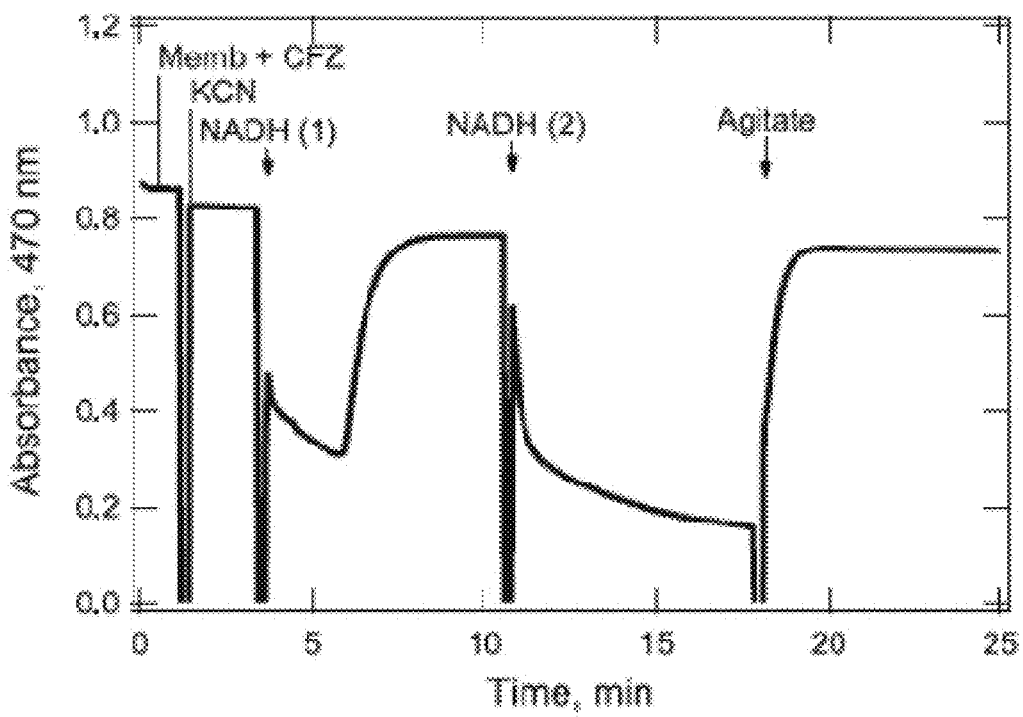
FIGS. 6A-6C, is a series of graphs illustrating the characterization of CFZ reduction and reoxidation in reactions with KCN-treated *M. smegmatis* membranes.
Figure 6B:
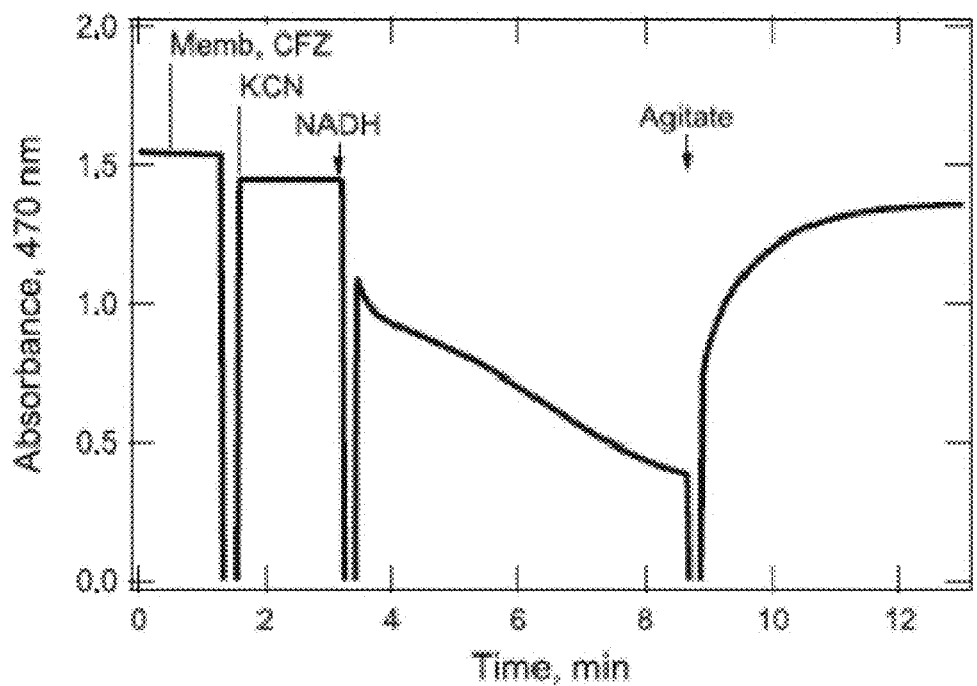

The reduction and oxidation of CFZ was characterized further in time course studies monitoring absorbance at 470 nm, the isosbestic point of the cationic and/neutral forms of CFZ. As illustrated in FIG. 6A, the absorbance change followed a time course similar to that shown in FIG. 4. There was a rapid decrease in absorbance upon NADH addition, which slowed and then returned to near the starting absorbance. The reversibility of the redox change was demonstrated when a second addition of NADH added to reoxidized CFZ induced an absorbance decrease. The second decrease did not reverse until the cuvette containing the reaction was manually shaken. Agitation likely raised the $O_2$ concentration in the reaction, which was depleted during the first cycle of reduction/oxidation. A similar change in absorbance was observed when the reactions were performed under anaerobic conditions and then exposed to air (data not shown).

To drive the $O_2$ concentration lower during the reaction, an incubation with a 2-fold higher concentration of NADH was incubated with twice the CFZ as illustrated in FIG. 6A. The higher concentration of NADH produced a prolonged slow phase with no spontaneous reoxidation until the cuvette was agitated. The return of absorbance after agitation fitted well to a first (pseudo) order process with an observed rate constant of $1.25 \pm 0.01$ min$^{-1}$ (error in fit). Assuming that agitation saturates the reaction with $O_2$ (250 µM at 1 atm pressure), the second order rate constant calculated for the reoxidation was 83 M$^{-1}$ s$^{-1}$.

Figure 6C:
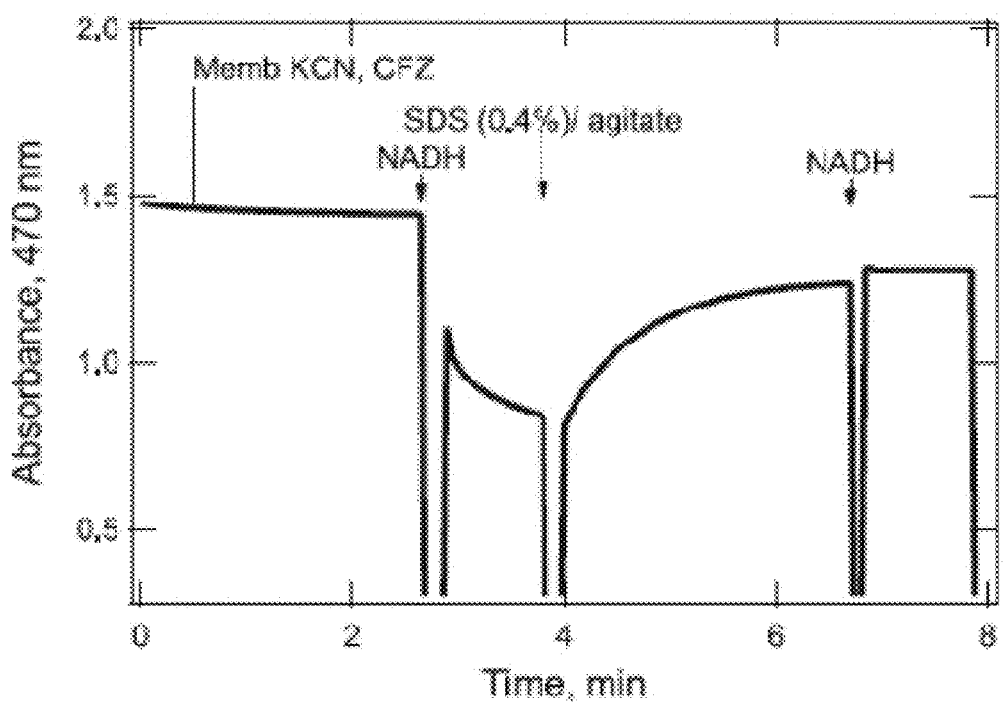

Reduced forms of phenazines tend to react spontaneously with $O_2$ (Barry, et al., 1957, *Nature* 179:1013-1015; and O'Connor, et al., 1995, *Drug Metab. Rev.* 27:591-614). The nonenzymatic oxidation of reduced CFZ in our reaction is illustrated in FIG. 6C, where SDS is introduced into the reaction to denature all enzymes. This reaction was performed as in FIG. 6A except that before reoxidation occurred, 0.5% SDS (final) was added to denature the system. As shown, SDS did not inhibit the reoxidation initiated by agitation upon the addition of the detergent. The reoxidation fitted well to a first order process with an observed rate constant $1.40 \pm 0.01$ min$^{-1}$, which is similar to that observed in the absence of SDS. CFZ reoxidized in the presence of SDS did not show an absorbance loss upon a further addition of NADH, confirming the denaturation of membrane enzymes. Similarly, SDS added at the beginning of a new reaction blocked CFZ reduction by NADH (data not shown). Reoxidation also was observed when CFZ, which had been chemically reduced by dithionite in absence of membranes, was exposed to air (data not shown).

Example 6

NADH Oxidation by Membranes in Presence of CFZ Produces ROS (Reactive Oxygen Species)

The spontaneous reoxidation of reduced CFZ by $O_2$ is likely to produce ROS, probably $O_2^-$. To show ROS was generated in the membrane assays, a coupled assay was devised to detect ROS. The detection system consisted of superoxide dismutase, HRP, and Amplex Red (a dye). Superoxide dismutase converts $O_2^-$ to $H_2O_2$ which reacts via HRP to oxidize Amplex Red to resorufin; the latter compound is quantified by absorbance at 563 nm. Because this coupled reaction measures product formation, it was not necessary to add KCN (KCN also inhibits HRP) to inhibit the electron transport chain. Thus, these studies also provide evidence on the ability of CFZ to abstract electrons from the respiratory chain while it is functioning.

As shown in FIG. 7A, NADH oxidation by log-phase membranes in the absence of CFZ showed a low rate of ROS production. The rate of ROS production increased markedly (11.5-fold) over the background rate upon addition of CFZ to the reaction. The rate of ROS production was similar to the rate of NADH oxidation measured in a parallel reaction monitored at 340 nm. In these reactions, the rate of electron flux through the respiratory chain was near maximal because the NADH concentration was close to saturating for the system. ROS production was sensitive to TPZ, consistent with the involvement of a respiratory chain enzyme in CFZ-mediated ROS production. Thus, CFZ is able to withdraw electrons from a normally functioning electron transport chain to produce ROS.

In FIG. 7B, the dependence of ROS production on the amount of CFZ in the reaction is illustrated. Rates of reaction in the absence and presence of CFZ were measured as in FIG. 7A. The data was plotted to show the proportion of the electron flux from NADH oxidation that went to the production of ROS. The percentage of NADH electrons producing resorufin was estimated using the extinction coefficients for NADH oxidation, a two-electron transfer, and resorufin production from Amplex Red, also a two-electron transfer. The rate of ROS production appeared to increase progressively before attaining a maximum at a CFZ/membrane protein ratio of 0.1-0.2 µg CFZ/µg membrane protein. Based on this maximum value, the resorufin production was ~18% of the rate of NADH consumption. Given that NADH oxidation by the respiratory chain is a continual process, this estimate suggests that significant levels of ROS production occur within *M. smegmatis* upon accumulation of CFZ in the membrane.

Example 7

Other Reductants

Menaquinone is a respiratory chain component that shuttles electrons/H$^+$ derived from the oxidation of NADH, or citric acid cycle intermediates succinate and malate, to the respiratory chain oxidoreductases. In *M. smegmatis*, menaquinone is reduced by at least three reactions: (1) NADH via NDH-2, (2) succinate via succinate dehydrogenase (producing fumarate which is the oxidized product), and (3) malate via malate:menaquinone oxidoreductase (producing oxaloacetate which is the oxidized product). The ability of NADH to reduce CFZ indicates that NDH-2 has a role in the reduction but does not eliminate the other respiratory chain enzymes (cytochrome $bc_1$ complex and terminal oxidases). If respiratory chain oxidoreductases other than NDH-2 reduce CFZ, succinate should be able to drive CFZ reduction. When succinate was substituted for NADH in our reactions neither CFZ reduction nor ROS production was observed. In experiments similar to those described in FIG. 6, 10 mM succinate did not produce CFZ reduction. The inability of succinate to drive ROS production is shown in FIG. 7A. Succinate dehydrogenase was active in isolated membranes as succinate could drive $O_2$ reduction and ATP synthesis. These results along with the inhibition CFZ-mediated NADH oxidation and ROS production by TPZ (FIGS. 4 and 7) strongly suggest that NDH-2, rather than the downstream oxidoreductase cytochrome $bc_1$ complex, cytochrome $aa_3$, or bd oxidase, is the respiratory chain oxidoreductase catalyzing CFZ reduction.

Example 8

Interaction of Purified NDH-2 with CFZ

To more conclusively show that NDH-2 is the respiratory enzyme able to reduce CFZ, studies were performed using purified recombinant NDH-2 instead of isolated membranes. Recombinant *M. tuberculosis* NDH-2 was previously expressed and purified (Yano, et al., 2006, *J. Biol. Chem.* 281:11456-11463). In FIG. 8A, the reduction of CFZ by purified NDH-2 is illustrated. This study was performed in a manner similar to that shown in FIG. 5, except that the incubation was performed under anaerobic conditions, and the reaction pH was lowered to 6.5 to increase CFZ solubility.

To perform this reaction (FIG. 8B), CFZ was added to the reaction buffer to achieve a concentration equivalent to 1.2 µg/ml. After a 40-min incubation, the absorption spectrum (CFZ in buffer) was taken. About two-thirds of CFZ remained soluble with spectra reflecting the cationic species. NADH was then added to the reaction to a final concentration of 0.2 mM. A spectrum taken after 10 min of incubation (+NADH) showed no change other than that attributed to NADH below 400 nm. The reaction was started by addition of purified NDH-2, which produced a rapid decrease in the visible spectrum, indicating reduction of CFZ. After 13 min of further incubation, the bleaching appeared complete. The cuvette was then exposed to air for 20 min. The spectrum after this incubation (air-oxidized) was consistent with the return of the oxidized CFZ. Finally, 0.1% SDS was added to the cuvette. This addition solubilized the precipitated material, which was in the oxidized form (data not shown). Thus, all of the CFZ was accounted for as oxidized after exposure to air.

In FIG. 8B, the generation of ROS by the incubation of purified recombinant NDH-2 with NADH and CFZ is shown. ROS formation was inhibited by TPZ added during the reaction. Taken together, both studies in FIG. 8 demonstrate that purified NDH-2 reduces CFZ similar to reactions with membranes.

Example 9

Figure 21A:
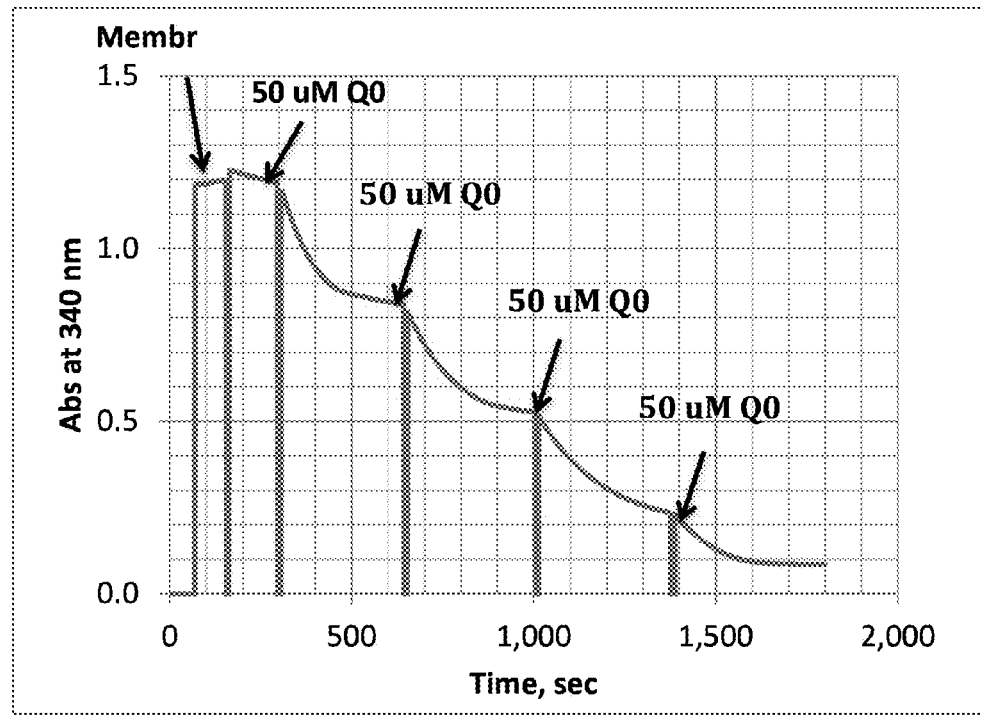
FIGS. 21A-21C, is a series of graphs illustrating that NDH-2 of E. faecalis membrane is responsible for production of ROS mediated by KS6.
Figure 21B:
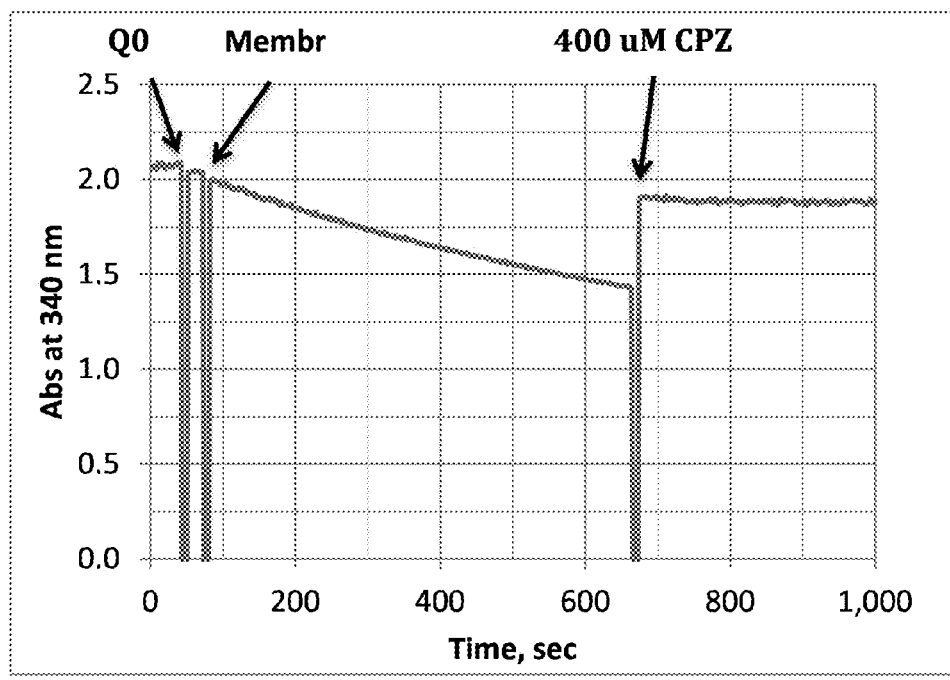
Figure 21C:
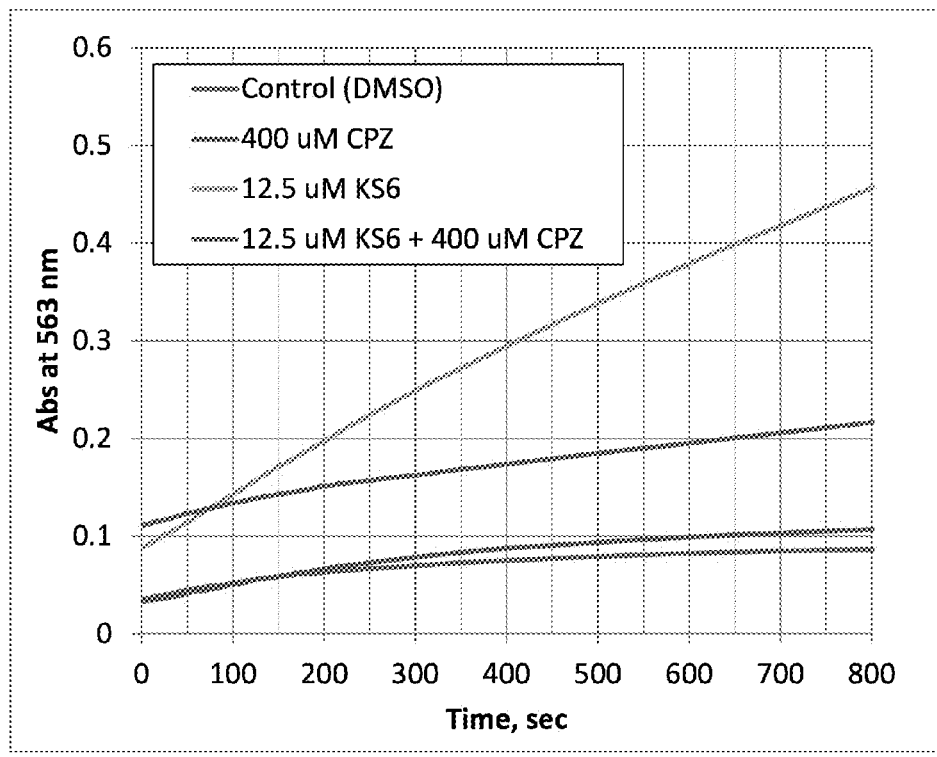

Effect of R-Iminophenazines on Respiratory Chain of Other Bacteria, Yeast, and Mammalian Mitochondria As illustrated in FIG. 2, CFZ could not restore NADH oxidase activity in *E. coli* membranes inhibited with KCN addition, indicating that CFZ was not reactive with membranes from all bacteria. To further investigate the species specificity of CFZ, studies similar to those shown in FIG. 2 were carried out using membranes from three Gram-negative bacteria (*E. coli, P. denitrificans,* and *P. aeruginosa*), a Gram-positive bacterium (*S. aureus*) and submitochondrial membranes from *S. cerevisiae* and rat mitochondria. Membranes prepared from the three Gram-negative organisms and rat mitochondria showed little, if any, restoration of NADH oxidation over background upon addition of CFZ (FIG. 9A) or KS6 (FIG. 9B). In contrast, membranes from *S. aureus* and submitochondrial membranes from *S. cerevisiae* demonstrated significant restoration of NADH oxidation over background. Similar results were also shown for ROS production using the assay described in FIG. 7. As illustrated in FIG. 21, KS6 strongly promoted ROS production by interacting with NDH-2, which is shown by complete inhibition by CPZ.

Figure 9:
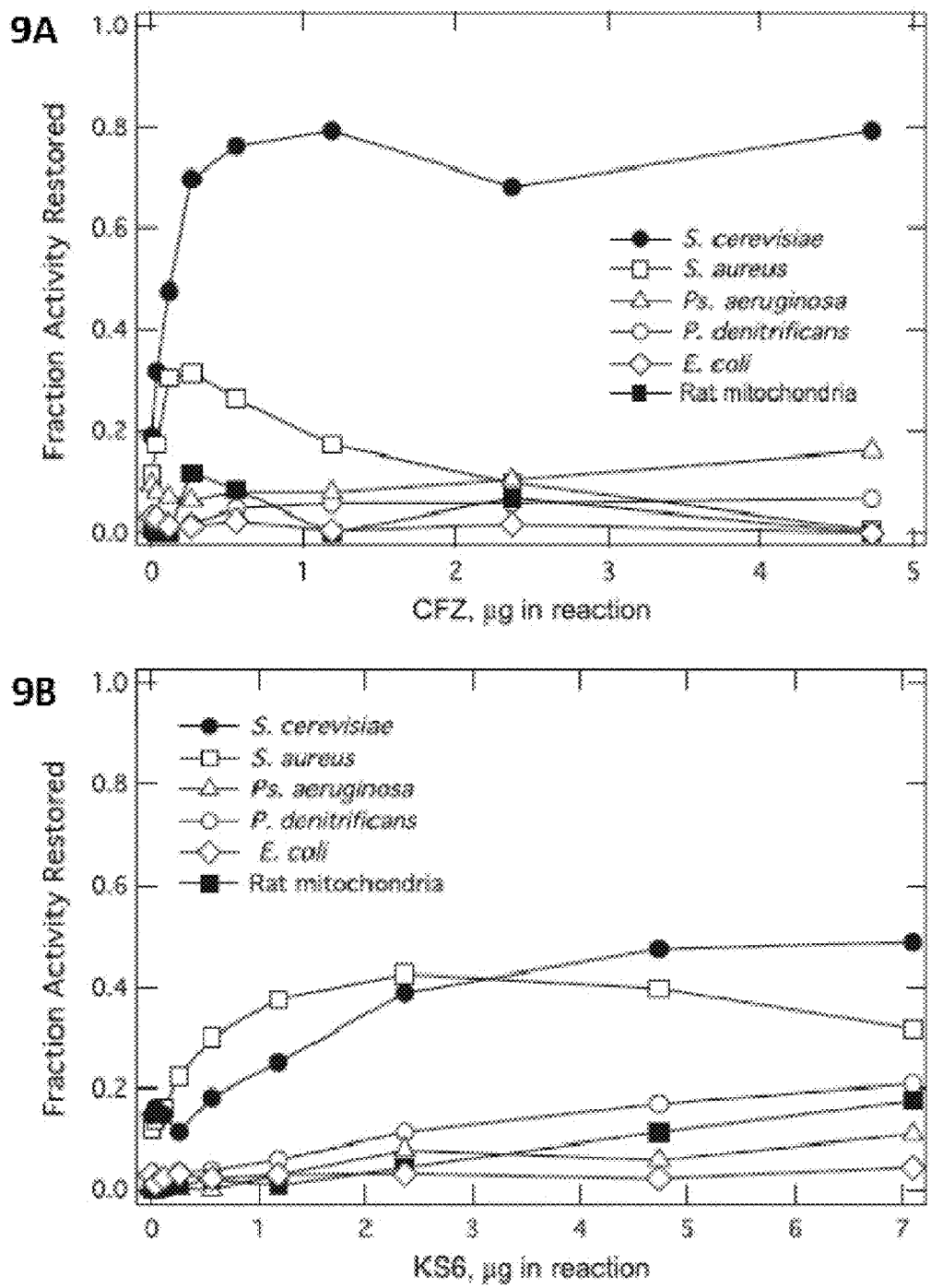
FIG. 9, comprising

The growth of *S. aureus* and *S. cerevisiae* are reported to be sensitive to CFZ (Oliva, et al., 2004, J. Antimicrob. Chemother. 53:435-440; and Rhodes, et al., 1973, Biochem. Pharmacol. 22:1047-1056). In the case of *S. aureus*, FIG. 9 shows that high levels of CFZ were inhibitory to CFZ-mediated NADH oxidation. This inhibitory effect was not seen with more soluble KS6 nor was it this dramatic with *M. smegmatis* membranes. The difference suggests that CFZ binding to some bacterial membranes can have significant disruptive effects on membrane enzyme activities.

Example 10

Effect of CFZ and Antioxidants on Growth of *M. smegmatis*

To show that ROS generation is responsible for inhibition of *M. smegmatis* growth in culture, the effect of antioxidants on CFZ-mediated growth inhibition was investigated. As shown in FIG. 10A, incorporation of CFZ into solid medium inhibits the growth of *M. smegmatis* in a dose-dependent manner. Virtually no colonies appeared on plates of agar containing the equivalent of ≥0.5 µg/ml CFZ after ≥4 days of incubation, whereas control plates with no CFZ averaged 670±100 colonies (FIG. 10A). As shown in FIG. 10B, growth inhibition at this CFZ concentration was prevented by addition of three different antioxidants, α-tocopherol (12.5 µg/ml), 4-hydroxy-TEMPO (5 mM), and N-acetylcysteine (5 and 10 mM). INH, an antibiotic used in the treatment of tuberculosis also completely inhibited *M. smegmatis* growth in this assay at a concentration of 10 µg/ml. In contrast to CFZ, the inhibitory effect of INH was not sensitive to antioxidants at the concentrations used in this study. Because INH activity is based on mycolic acid synthesis inhibition, these studies strongly suggest the production of ROS in the mechanism of action of CFZ.

Example 11

Antimicrobial Activities

The antimicrobial activities of CFZ and KS6 are illustrated in Table 1.

TABLE 1

|  | MIC, μM | |
|---|---|---|
|  | CFZ | KS6 |
| *Bacillus thuringiensis* | 5 | 3.1 |
| *Staphylococcus aureus* MRSA | 2.5 | 3.1 |
| *Enterococcus faecalis* | 10 | 12.5 |
| *Enterococcus faecium* | 10 | 25 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I), or a salt or solvate thereof:

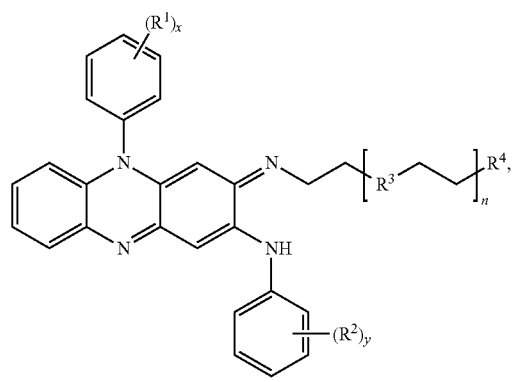

(I)

wherein:
each occurrence of $R^1$ and $R^2$ is independently selected from the group consisting of F, Cl, Br, I, CN, $NO_2$, $OR^5$, $SR^5$, $S(=O)R^6$, $S(=O)_2R^6$, $NHS(=O)_2R^6$, $C(=O)R^5$, $OC(=O)R^5$, $CO_2R^5$, $OCO_2R^6$, $N(R^5)_2$, $C(=O)N(R^5)_2$, $OC(=O)N(R^5)_2$, $NHC(=O)NH(R^5)$, $NHC(=O)R^5$, $NHC(=O)OR^5$, $C_1$-$C_6$ alkyl, $C_1$-$C_6$ fluoroalkyl and $C_1$-$C_6$ heteroalkyl;

each occurrence of $R^3$ is independently selected from the group consisting of $N(R^5)$, $CH_2N(R^5)$, O, and $CH_2O$;

$R^4$ is selected from the group consisting of $(CH_2)_mOR^5$, and $(CH_2)_mN(R^5)_2$;

each occurrence of $R^5$ is independently selected from the group consisting of H, $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of $R^6$ is independently selected from the group consisting of $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of x and y is independently selected from the group consisting of 0, 1, 2, and 3;

n is an integer ranging from 2 to 4; and m is an integer ranging from 0 to 3.

2. The compound of claim 1, wherein each occurrence of $R^1$ and $R^2$ is independently selected from the group consisting of F, Cl, Br, I, CN, $NO_2$, COOH, $C(=O)NH_2$ and $C(=O)NH$—$C_1$-$C_6$ alkyl.

3. The compound of claim 1, wherein $R^4$ is selected from the group consisting of OH and $NH_2$.

4. The compound of claim 1, wherein each occurrence of $R^3$ is independently selected from the group consisting of N(H), $CH_2N(H)$, O, and $CH_2O$.

5. The compound of claim 1, which is selected from the group consisting of:
(Z)-3-((2-(2-(2-aminoethoxy)ethoxy)ethyl)imino)-N,5-bis(4-chlorophenyl)-3,5-dihydrophenazin-2-amine;
(Z)—$N^1$-(2-aminoethyl)-$N^2$-(2-((10-(4-chlorophenyl)-3-((4-chlorophenyl)amino)phenazin-2(10H)-ylidene)amino)ethyl)ethane-1,2-diamine;
(Z)—$N^1$-(2-aminoethyl)-$N^2$-(2-((10-(phenyl)-3-((phenyl)amino)phenazin-2(10H)-ylidene)amino)ethyl)ethane-1,2-diamine;
(Z)—$N^1$-(3-((10-phenyl-3-(phenylamino)phenazin-2(10H)-ylidene)amino)propyl)butane-1,4-diamine;
combinations thereof, and a salt or solvate thereof.

6. The compound of claim 1, which is part of a pharmaceutical composition further comprising at least one pharmaceutically acceptable carrier.

7. A compound of formula (I), or a salt or solvate thereof:

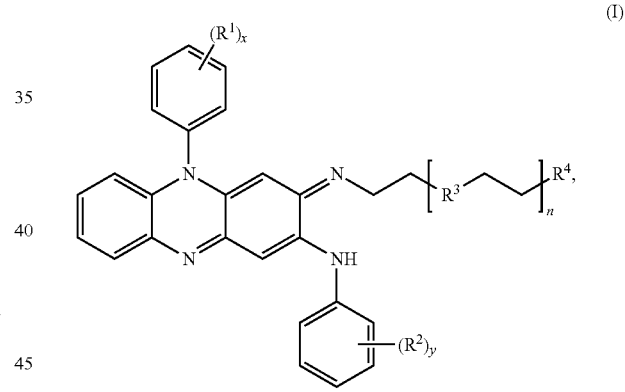

(I)

wherein:
each occurrence of $R^1$ and $R^2$ is independently selected from the group consisting of F, Cl, Br, I, CN, $NO_2$, $OR^5$, $SR^5$, $S(=O)R^6$, $S(=O)_2R^6$, $NHS(=O)_2R^6$, $C(=O)R^5$, $OC(=O)R^5$, $CO_2R^5$, $OCO_2R^6$, $N(R^5)_2$, $C(=O)N(R^5)_2$, $OC(=O)N(R^5)_2$, $NHC(=O)NH(R^5)$, $NHC(=O)R^5$, $NHC(=O)OR^5$, $C_1$-$C_6$ alkyl, $C_1$-$C_6$ fluoroalkyl and $C_1$-$C_6$ heteroalkyl;

each occurrence of $R^3$ is independently selected from the group consisting of $N(R^5)$, $CH_2N(R^5)$, O, and $CH_2O$;

$R^4$ is $(CH_2)_mNR^5(C=NR^5)N(R^5)_2$;

each occurrence of $R^5$ is independently selected from the group consisting of H, $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of $R^6$ is independently selected from the group consisting of $C_1$-$C_6$ alkyl, $C_1$-$C_6$ fluoroalkyl, $C_1$-$C_6$ heteroalkyl, $C_3$-$C_{10}$ cycloalkyl, $C_2$-$C_{10}$ heterocycloalkyl, aryl, heteroaryl, $C_1$-$C_4$ alkyl-($C_3$-$C_{10}$ cycloalkyl), $C_1$-$C_4$ alkyl-($C_2$-$C_{10}$ heterocycloalkyl), $C_1$-$C_4$ alkyl-(aryl), and $C_1$-$C_4$ alkyl-(heteroaryl);

each occurrence of x and y is independently selected from the group consisting of 0, 1, 2, and 3;

n is an integer ranging from 0 to 4; and m is an integer ranging from 0 to 3.

8. The compound of claim 7, wherein each occurrence of $R^1$ and $R^2$ is independently selected from the group consisting of F, Cl, Br, I, CN, $NO_2$, COOH, C(=O)$NH_2$ and C(=O)NH—$C_1$-$C_6$ alkyl.

9. The compound of claim 7, wherein each occurrence of $R^3$ is independently selected from the group consisting of N(H), $CH_2$N(H), O, and $CH_2$O.

10. The compound of claim 7, which is selected from the group consisting of:

- (Z)-1-(2-((10-(4-chlorophenyl)-3-((4-chlorophenyl)amino)phenazin-2(10H)-ylidene)amino)ethyl)guanidine;
- (Z)-1-(2-((10-(phenyl)-3-((phenyl)amino)phenazin-2(10H)-ylidene)amino)ethyl)guanidine;
- (Z)-1-(4-((3-((10-phenyl-3-(phenylamino)phenazin-2(10H)-ylidene)amino)propyl)amino)butyl)guanidine;
- (Z)-1-(2-(2-(2-((10-(4-chlorophenyl)-3-((4-chlorophenyl)amino)phenazin-2(10H)-ylidene)amino)ethoxy)ethoxy)ethyl)guanidine;
- (Z)-1-(2-(2-(2-((10-(4-nitrophenyl)-3-((4-nitrophenyl)amino)phenazin-2(10H)-ylidene)amino)ethoxy)ethoxy)ethyl)guanidine;
- (Z)-1-(2-(2-(2-((10-(phenyl)-3-((phenyl)amino)phenazin-2(10H)-ylidene)amino)ethoxy)ethoxy)ethyl)guanidine;
- (Z)-1-(2-(2-(2-((10-(4-carboxyphenyl)-3-((4-carboxyphenyl)amino)phenazin-2(10H)-ylidene)amino)ethoxy)ethoxy)ethyl)guanidine;
- (Z)-1-(2-(2-(2-((10-(4-hydroxyphenyl)-3-((4-hydroxyphenyl)amino)phenazin-2(10H)-ylidene)amino)ethoxy)ethoxy)ethyl)guanidine;
- (Z)-1-(2-(2-(2-((10-(4-carbamoylphenyl)-3-((4-carbamoylphenyl)amino)phenazin-2(10H)-ylidene)amino)ethoxy)ethoxy)ethyl)guanidine;
- (Z)-1-(2-((10-(4-nitrophenyl)-3-((4-nitrophenyl)amino)phenazin-2(10H)-ylidene)amino)ethyl)guanidine;
- (Z)-1-(2-((10-(4-carboxyphenyl)-3-((4-carboxyphenyl)amino)phenazin-2(10H)-ylidene)amino)ethyl)guanidine;
- (Z)-1-(2-((10-(4-carbamoylphenyl)-3-((4-carbamoylphenyl)amino)phenazin-2(10H)-ylidene)amino)ethyl)guanidine;
- (Z)-1-(2-((10-(4-(N-methyl)carbamoylphenyl)-3-((4-(N-methyl)carbamoylphenyl)amino)phenazin-2(10H)-ylidene)amino)ethyl)guanidine;
- (Z)-1-(2-((10-(4-hydroxyphenyl)-3-((4-hydroxyphenyl)amino)phenazin-2(10H)-ylidene)amino)ethyl)guanidine;

combinations thereof, and a salt or solvate thereof.

11. The compound of claim 7, which is part of a pharmaceutical composition further comprising at least one pharmaceutically acceptable carrier.

* * * * *